(12) United States Patent
Pribilla et al.

(10) Patent No.: US 8,470,523 B2
(45) Date of Patent: Jun. 25, 2013

(54) METHOD FOR DETECTING INTRACELLULAR INTERACTION BETWEEN BIOMOLECULES

(75) Inventors: Iris Pribilla, Berlin (DE); Hervé Bazin, Villeneuve les Avignon (FR); Sraboni Ghose, Chusclan (FR); Norbert Tinel, Lunel Viel (FR); Michel Fink, Bagnols sur Ceze (FR); Eric Trinquet, Pont Saint Esprit (FR); Gérard Mathis, Bagnols sur Ceze (FR)

(73) Assignee: CIS BIO International, Saclay (FR)

( * ) Notice: Subject to any disclaimer, the term of this patent is extended or adjusted under 35 U.S.C. 154(b) by 874 days.

(21) Appl. No.: 12/065,706

(22) PCT Filed: Sep. 4, 2006

(86) PCT No.: PCT/FR2006/050838
§ 371 (c)(1),
(2), (4) Date: Aug. 11, 2008

(87) PCT Pub. No.: WO2007/028921
PCT Pub. Date: Mar. 15, 2007

(65) Prior Publication Data
US 2009/0215106 A1 Aug. 27, 2009

(30) Foreign Application Priority Data
Sep. 5, 2005 (FR) ..................................... 05 09060

(51) Int. Cl.
*C12Q 1/00* (2006.01)

(52) U.S. Cl.
USPC ................... 435/4; 435/29; 435/183; 435/195

(58) Field of Classification Search
USPC ........................................ 435/4, 29, 183, 195
See application file for complete search history.

(56) References Cited

U.S. PATENT DOCUMENTS

| | | | |
|---|---|---|---|
| 4,637,988 A | 1/1987 | Hinshaw et al. |
| 4,670,572 A | 6/1987 | Hinshaw et al. |
| 4,761,481 A | 8/1988 | Hale et al. |
| 4,794,191 A | 12/1988 | Hinshaw et al. |
| 4,801,722 A | 1/1989 | Hinshaw et al. |
| 4,837,169 A | 6/1989 | Toner |
| 4,859,777 A | 8/1989 | Toner |
| 5,032,677 A | 7/1991 | Hale et al. |
| 5,055,578 A | 10/1991 | Hale et al. |
| 5,106,957 A | 4/1992 | Hale et al. |
| 5,116,989 A | 5/1992 | Hale et al. |
| 5,202,423 A | 4/1993 | Kankare et al. |
| 5,316,909 A | 5/1994 | Xu |
| 5,324,825 A | 6/1994 | Kankare et al. |
| 6,924,119 B2 | 8/2005 | Umezawa |
| 2002/0081617 A1 | 6/2002 | Buranda et al. |
| 2004/0082080 A1 | 4/2004 | Wolf et al. |

FOREIGN PATENT DOCUMENTS

| | | |
|---|---|---|
| EP | 321 353 | 5/1992 |
| EP | 180 492 | 6/1993 |
| EP | 569 496 B1 | 9/1994 |
| EP | 601 113 | 1/1997 |
| EP | 403 593 | 3/1997 |
| FR | 2 840 611 | 12/2003 |
| WO | WO 01/96 877 | 12/2001 |
| WO | WO 02/083937 A2 | 10/2002 |
| WO | WO 2004 057333 A1 | 7/2004 |
| WO | WO 2004/072232 A2 | 8/2004 |

OTHER PUBLICATIONS

He et al. "A flow cytometric method to detect protein-protein interaction in living cells by directly visualizing donor fluorophore quenching during CFP-YFP fluorescence resonance energy transfer (FRET)", Cytometery Part A, 2003, 55A:71-85.*
Nitin et al. "Peptide-linked molecular beacons for efficient delivery and rapid mRNA detection in living cells", Nucleic Acids Research, 2004, 32(6):e58:1-8.*
Enomoto et al. "High throughput screening for human interferon-gamma production inhibitor using homogenous time-resolved fluorescence", J of Biomolecular Screening, 2000, 5(4):263-268.*
Cha et al. "Atomic scale movement of the voltage-sensing region in a potassium channel measured via spectroscopy", Nature, 1999, 402:809-813.*
Griffin et al. "Specific covalent labeling of recombinant protein molecules inside live cells", Science, 1998, 281:269-272.*
Bogdanov et al. "Transmembrane protein topology mapping by the substituted cysteine accessibility method (SCAMtm): application to lipid-specific membrane protein topogenesis", Methods, 2005, 36:148-171.*
Sato et al. "Fluorescent indicators for imaging protein phosphorylation in single living cells", Nature Biotechnology, 20:287-294.*
Shi et al. "Development of a tandem protein trans-splicing system based on native and engineered split inteins", J. Am. Chem. Soc., 2005, 127:6198-6206.*
Johnson "Fluorescent probes for living cells", Histochemical Journal, 1998, 30:123-140.*
Bazin H et al, "Time resolved amplification of cryptate emission: a versatile technology to trace biomolecular interactions.", Journal of Biotechnology, Jan. 2002, vol. 82, No. 3, pp. 233-250, XP002385176.
Maurel D et al, "Cell surface detection of membrane protein interaction with homogeneous time-resolved fluorescence resonance energy transfer technology", Analytical Biochemistry, Academic Press, New York, NY, US, vol. 329, No. 2, Jun. 15, 2004, pp. 253-262, XP004509821.
Moens P D J et al, "Detection of tryptophan to tryptophan energy transfer in proteins", Protein Journal, Kluwer Academic/Plenum Publishers, Dordrecht, NL, vol. 23, No. 1, Jan. 1, 2004, pp. 79-83, XP002328973.
Hong Catherine A et al, "Development of a high throughput time-resolved fluorescence resonance energy transfer assay for TRAF6 ubiquitin polymerization.", Assay and Drug Development Technologies, Feb 2003, vol. 1, No. 1 Pt 2, pp. 175-180, XP002427176.
Takesono et al. Journal of Cell Sciences, 115, 3039-3048, (2002).
Revue de John Comley, DDW, summer 2005, pp. 31-53.
Janetopoulos et al. Science (2001) 291 : 2408-2411.
Vilardaga et al. Nature Biotech. (2003) 21 : 807-812.
Nikolaev et al., JBC, vol. 279, N° 36, pp. 37215-37218, 2004.
Tanimura et al. JBC, vol. 279, N° 37, pp. 38095-38098, 2004.
Milligan G Eur J Pharm Sci. Mar. 2004;21(4):397-405.
Boute N et al. Trends Pharmacol Sci. Aug. 2002; 23(8):351-4.
Trugnan G. et al. Med Sci (Paris). Nov. 2004;20(11):1027-34.

(Continued)

*Primary Examiner* — Susan Hanley

(74) *Attorney, Agent, or Firm* — Millen, White, Zelano & Branigan, P.C.

(57) ABSTRACT

The invention relates to a quantitative non-microscopic method of detecting intracellular interactions between biomolecules in living cells, in response to a biological or pharmacological stimulation, by a time-resolved proximate energy transfer effect between two members of a fluorescence donor/acceptor pair.

10 Claims, 12 Drawing Sheets
(1 of 12 Drawing Sheet(s) Filed in Color)

OTHER PUBLICATIONS

Ozawa T, Current Opinion in Chemical Biology, 2001, N° 5, pp. 578-583 pour revue.
Eglen R, Assay and Drug Develop. Technologies, 2002, vol. 1, pp. 97-104.
Dirks et al. 2003, Methods, Jan. 29, N° 1, pp. 51-57.
Tsuji et al. Biophys J. Jul. 2001; 81(1):501-15.
Poole R. et al. Org. Dans Biomol. Chem, 2005, 3, 1013-1024 "Synthesis and characterisation of highly emissive and kinetically stable lanthanide complexes suitable for usage in cellulo".
Klepper A. et al. (2003) in Nature Biotechnology, vol. 21, p. 86.
Muir T.W. et al. (2003) J. Am. Chem. Soc. 2003, 125, 7180-7181.
B.A.Griffin et al. (1998) Science. 1998, 281, 269-271.
S.A. Adams et al. (2002) J. Am. Chem. Soc. 2002, 124, 6063-6076.
E.G. Guignet et al. (2004), Nature biotech., 2004, 22, 440-444.
C. M. McCann et al. (2005), Biotechnique (2005), 38, 945-952.
Taki et al (2004) Protein Engeneering, Design Selection, 2004,17, 119-12.
Pljevaljcic G. et al. (2004) ChemBioChem, 5; 265-269.
T. Higuchi et V. Stella in "Pro-drugs as Novel Delivery Systems", vol. 14 of the A.C.S. Symposium Series, American Chemical Society (1975).
Nielsen et Bundgaard, Int. J. of Pharmacy. 39(1984) 75-85.
Langel et al. Bioconj. Chem. (2000), 11, 619-626.
Wender et al. Arginine-based molecular transporters. Org. Lett. (2003), 5(19), 3459-3462.
The design, synthesis, and evaluation of molecules that enable or enhance cellular uptake: peptoid molecular transporters. Wender et al. Proc Natl Acad Sci U S A. (2000), 13003-8.
Fernandez-Carneado J. et al. J. Am. Chem. Soc. 2005, 127, 869-874.
3'-end conjugates of minimally phosphorothioate-protected oligonucleotides with 1-O-hexadecylglycerol: synthesis and anti-ras activity in radiation-resistant cells. Rait et al. Bioconj. Chem. (2000), 11, 153-160.
Sakai N. J. Cell Bio. (1997) 139, 1465-1476.

* cited by examiner

No FRET : Calcineurin inactive form

FRET : Calcineurin active form

ST : Snap-Tag labelled with fluorophore 1
HT : Halo-Tag labelled with fluorophore 2

Image 1: time-resolved acquisition
Image 2: developing Hoechst 33342
Image 3: transmitted light
Image 5: overlapping images 1 and 2
Image 5: time-resolved negative control

DY647 + BG + NH2

DY647 + BG + COOH

SEQUENCE LISTING

```
<160> NUMBER OF SEQ ID NOS: 8

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid

<400> SEQUENCE: 1

Cys Cys Xaa Xaa Cys Cys
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Lys Pro Gln Gln Phe Met
1               5

<210> SEQ ID NO 3
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 3

Cys Ala Ala Xaa
1

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcggatatcg ccaccatggg atcc                                            24

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acttaattaa ctgcaggccg gccagc                                          26

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gttctgattt aatctgtatc a                                               21

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Arg Arg Arg Arg Arg Arg Arg Arg
1               5

<210> SEQ ID NO 8
<211> LENGTH: 7
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 8

Arg Arg Arg Arg Arg Arg Arg
1               5
```

METHOD FOR DETECTING INTRACELLULAR INTERACTION BETWEEN BIOMOLECULES

SEQUENCE LISTING

The instant application contains a Sequence Listing which has been submitted in ASCII format via EFS-Web and is hereby incorporated by reference in its entirety. Said ASCII copy, created on Jun. 13, 2011, is named LOM0054.txt and is 2,232 bytes in size.

The present invention relates to a quantitative non-microscopic method of detecting intracellular interactions between biomolecules, on living cells, in response to a biological or pharmacological stimulation, by a time-resolved proximate energy transfer effect between two members of a fluorescence donor/acceptor pair, and to its applications such as, in particular, the high-throughput screening of molecules and the detection of intracellular signaling pathways.

TECHNICAL FIELD AND PRIOR ART

Molecules with pharmacological activity (e.g. drugs) act on molecular targets located either on the plasma membrane or inside the living cells themselves. To select and optimize candidate molecules in the search procedures within the pharmaceutical industry, it is necessary to determine their molecular actions, as far as possible in a native environment so as to integrate the modulations that may be introduced by interactions between different partners. From a more fundamental point of view, for physiological or pathological conditions, it is important to have access to cellular models in which the direct interactions between biomolecules that are involved in intracellular signaling pathways can easily be studied, characterized and quantified [cf., for example, Takesono et al., Journal of Cell Sciences, 115, 3039-3048 (2002)]. This desire to understand mechanisms of action in the native condition explains why tests on cells are increasingly being used in the primary screenings of molecules. At the present time, however, the high-throughput screening techniques mainly allow detection of the final products of biological events, such as the production of second messengers. In this case the cells must be lyzed in order to allow access to the intracellular target molecule which has to be assayed. Very few kinetic observations are currently possible and rare events easily go undetected. Novel approaches using the techniques of microscopy or imaging on living cells provide access to the dynamic and kinetic parameters of one or more biomolecules of interest in their native environment, in response to a stimulation. These techniques are based on studies of the movements of these biomolecules in response to a stimulus. Analysis of these displacements involves image processing to give access, a posteriori and by indirect methods, to arbitrary values that enable the biological events in question to be quantified.

These microscopy techniques consist in determining the location of a molecular target and following any changes in location. For these approaches the molecular target is generally fused with a fluorescent protein that may belong to the GFP family. Such techniques of direct visualization inside a cell are performed with the aid of a conventional fluorescence microscope, confocal microscopes or novel platforms that integrate microscopy and image acquisition. Such platforms are used e.g. in TRANSFLUOR technology (Molecular Devices) or on instruments such as OPERA (Evotech Technologies) or In Cell analyser (GE Healthcare) (cf. review by John Comley, DDW, summer 2005, pp 31-53).

However, the use of such technologies is limited by numerous disadvantages:

Microscopic studies are tricky and difficult to automate and require complex image analysis tools, specific softwares and very experienced users; they also require a great deal of time.

Image analysis is complicated and often a source of errors, and these technologies are difficult to reproduce and rather unreliable (low value of the parameter Z').

They make it possible to follow biological events in living cells with a moderate throughput of molecule screening that limits their use in the primary screening steps.

The visualized effects are generally downstream of the signaling cascade.

It is for these main reasons that these techniques are not compatible with high-throughput molecule screening.

Apart from these features, these technologies serve to qualify one or more cellular events, which most frequently are the consequence of a cascade of earlier events, giving indirect access to the event which it is desired to measure. Furthermore, these techniques do not provide direct information on the interactions between biomolecules or on the conformational changes within one and the same molecule, both of which are direct indicators of the biological event which it is desired to detect and quantify.

Nowadays, the intracellular technologies that make it possible to characterize the interactions between biomolecules or the conformational changes within one and the same biomolecule, both of these being evidence of biological events, are based on the technology of energy transfer (FRET) between different fluorescent proteins such as the green fluorescent protein (GFP) and its different mutants. By way of example, two protein variants of GFP (CFP and YFP) form a compatible pair for establishing a FRET. They can be fused with the target proteins of interest and be expressed in living cells. Numerous events involving interaction or conformational changes between proteins labeled in this way have been detected using a FRET method (cf. Janetopoulos et al., SCIENCE (2001) 291: 2408-2411, Vilardaga et al., NATURE BIOTECH. (2003) 21: 807-812, and WO 2004 057333 A1).

The two variants of GFP (CFP and YFP) can also be expressed in living cells as fusion products with one and the same target protein. This biomolecule, doubly fused with the two variants of GFP, is defined as a biosensor. A biosensor is capable of adopting different conformations depending on the changes in biological environment, it being possible for these conformational changes to be monitored by a FRET method. Such biomolecules can be used to monitor numerous cellular events such as the production of cAMP, IP3 or cGMP (cf. Nikolaev et al., JBC, vol. 279, no. 36, pp 37215-37218, 2004, Tanimura et al., JBC, vol. 279, no. 37, pp 38095-38098, 2004, and patent U.S. Pat. No. 6,924,119 B2).

However, the use of these fluorescent proteins has certain major disadvantages:

The overlap spectra of the two fluorescent molecules (CFP and YFP) are broad and cause a strong parasitic excitation of the acceptor (YFP) at the wavelengths used to excite the donor (CFP). This parasitic contamination induces a strong background noise which reduces the signal-to-noise ratio to a value below 1.5. Such small differences in modulation prevent these techniques from being used satisfactorily in high-throughput molecule screening.

At the wavelengths used to detect the FRET with these fluorescent proteins, an autofluorescence intrinsic to the cells perturbs the FRET reading.

Microscopic analyses may be necessary to reveal subtle changes in FRET signals. Such analyses then exhibit the same disadvantages as those described above for the first detection approach.

The limited number of variants of GFP restricts the use of such proteins to applications where the proximate changes are consistent with the Förster radius (Ro) of the CFP/YFP pair.

These proteins are fused with the target proteins. The fluorescence of these proteins is detected as soon as the cell expresses it, and it cannot be triggered or controlled by the experimenter without providing much more complex expression systems.

An alternative to FRET using GFP or its variants, which can be controlled by the experimenter, is the use of a molecule which generates bioluminescence, referred to as BRET. A BRET process can take place in living cells between proteins labeled respectively with luciferase and GFP. It has been possible to measure several intracellular protein interactions by fusing luciferase with one of the partners and GFP with the other (cf. Milligan G., Eur. J. Pharm. Sci. 2004 March; 21(4): 397-405, Boute N. et al., Trends Pharmacol. Sci. 2002 August; 23(8): 351-4, and Trugnan G. et al., Med. Sci. (Paris), 2004 November; 20(11): 1027-34). The energy transfer process is initiated when the substrate for the enzyme luciferase is introduced into the cellular preparation to be tested. The luciferase produces a light which, in the case of a protein interaction that allows a close proximity between the two partners, excites the GFP. The fluorescence signal emitted by the GFP is then measured.

In the same way as for the CFP/YFP pair, numerous disadvantages limit the use of the luciferase/GFP pair in high-throughput screening (HTS):

The signal-to-noise ratio of the BRET tests is rather low.

The fluorescence signal can easily be masked by an autofluorescence of the test products. BRET technology is not sufficiently robust for screening molecules because of the low stability of the signal over time, which leaves a very short reading window that is not very compatible with high-throughput molecule screening.

Another series of technologies for studying the interactions between biomolecules consists in using a functional complementation process. The biomolecules of interest are fused with 2 inactive fragments of a 3rd protein. When the direct interaction between the biomolecules of interest takes place, the 2 inactive fragments of the 3rd protein then reconstitute, by direct interaction or by a more complex process of protein splicing, a functional 3rd protein whose activity can be measured. This protein, whose activity has been restored by the interaction between the biomolecules of interest, can be a luciferase, in which case the measured activity is a luminescence signal, a fluorescent protein such as GFP (cf. Ozawa T., Current Opinion in Chemical Biology, 2001, no. 5, pp 578-583 for review) or an enzyme such as β-galactosidase, whose enzymatic activity is measured by a colorimetric method (cf. Eglen R., ASSAY and Drug Develop. Technologies, 2002, vol. 1, pp 97-104) and the Path Hunter® method from DISCOVER.

The main disadvantage of these approaches using functional complementation lies in the fact that the measurement of interaction between biomolecules is dependent on a perfect reconstitution of the 3rd protein in its active form, such as β-galactosidase, and sometimes requires displacement of the interaction complex into a cellular compartment other than that in which the biomolecules normally interact. Finally, functional complementation is an indirect method of characterizing an interaction between biomolecules of interest, where the interaction is detected by measurement of an enzymatic activity. The use of functional complementation is more complex in the case of a single biosensor type biomolecule.

Depending on the intrinsic properties of the proteins used in these energy transfer processes, the technologies using fluorescent proteins such as GFP (or its other variants) or bioluminescent proteins such as luciferase do not allow a great flexibility in the choice of the donor/acceptor pair involved in the energy transfer process.

The use of particular fluorescent molecules called "quantum dots" offers a much larger number of possible donor/acceptor pairs, makes it possible to work over a broader range of excitation wavelengths and, by combining different pairs, enables different interactions between biomolecules to be measured concomitantly (multiplex approach). However, it is difficult to label the biomolecules specifically with these compounds in the cell.

The use of fluorescent organic molecules for intracellular FRET applications has been described e.g. for the visualization of messenger RNAs in living cells. The interaction involved in this case is based on a match between the target messenger RNA and antisense oligonucleotide sequences labeled with fluorescent organic molecules (cf. Dirks et al. 2003, METHODS, January 29, no. 1, pp 51-57, and Tsuji et al., Biophys. J. 2001 July; 81(1): 501-15). The information obtained in this case is not quantitative since it relies on detection by microscopy. Furthermore, it does nothing to qualify an interaction between two biomolecules of interest and serves only to reveal the presence of a messenger RNA of interest.

There is a genuine need in the scientific community for novel tools and methods for studying the biological phenomena in living cells, while avoiding the disadvantages associated with the use of the known techniques.

DESCRIPTION OF THE INVENTION

The present method of quantitative and direct analysis of intracellular interactions on living cells without the aid of microscopy exploits the properties of long-lived fluorescent compounds in order to effect a detection by time-resolved FRET (TR-FRET).

This technique uses a first long-lived donor fluorescent compound and one or more acceptor fluorescent compounds that possess spectral characteristics compatible with the first fluorescent compound.

This time-resolved FRET measurement offers two ways of avoiding the problems of background noise and of autofluorescence of the cells and possibly the test molecules:

the long lifetime of the fluorescent compound, preferably greater than 100 nanoseconds, makes it possible to define a time window for measurement in which the emissions of the short-lived fluorescent compounds are not present;

the measurement of two tracers, one of them as a reference, makes it possible to compensate the effects of residual autofluorescence by using the fluorescence emission ratio between the two tracers as the reading.

By virtue of its sensitivity, its specificity, its robustness and its molecular resolution, TR-FRET makes it possible, in the method of the invention, to eliminate all the disadvantages observed in living cells of FRET applications between CFP/YFP or BRET applications with luciferase and GFP, particularly:

the wide choice of fluorescent compounds and the time-resolved reading make it possible to eliminate the strong parasitic excitation of the acceptor at the wavelengths used to excite the donor;

the time-resolved reading makes it possible to remove the effects of autofluorescence of the cells and the test products;

the amplitude of the TR-FRET signals is larger than that measured with FRET techniques using dyes/fluorescent proteins.

The TR-FRET technique has so far never been used in living cells. This is due to numerous technical obstacles which the Applicant has been able to overcome.

One of the major technical problems involved in carrying out this technique in a living cell lies in the fact that the majority of fluorescent compounds are often very hydrophilic and do not cross the plasma membrane. Another problem is associated with the fact that these compounds are sensitive to their environment and, in particular, their fluorescence yield can be greatly affected in a biological medium. Finally, the Applicant had to overcome another obstacle in order to label biomolecules present in the cell with fluorescent compounds introduced outside the cell, without affecting the biological integrity of the cells.

The method of the invention makes it possible to circumvent these obstacles and thus provides effective means of studying biological phenomena inside living cells.

The method of the invention makes it possible to detect and quantify interactions or conformational modifications between biomolecules on living cells in response to a specific stimulation.

The invention relates to a method of detecting interactions between biomolecules or a translocation or conformational change of biomolecules in living cells, comprising the following steps consisting in:

1) labeling a first biomolecule, in the living cell, with a first fluorescent compound having a long fluorescence lifetime;

2) labeling at least one second biomolecule, in the living cell, with a second fluorescent compound;

3) subjecting the living cells to a specific stimulation adapted to the biological response to be studied, in the presence or absence of a bank of test molecules with pharmacological activity (potential candidates for future drugs);

4) subjecting the living cells to a light source whose wavelength excites said first long-lived fluorescent compound;

5) measuring the intensity of the fluorescence emitted by said first and second fluorescent compounds, and calculating the ratio between the fluorescence intensities of said first fluorescent compound and said second fluorescent compound, or measuring the lifetime of the first or second fluorescent compound; and 6) comparing the measured signals with those obtained before stimulation of the cells.

Luminous excitation of the living cells can be effected by methods well known to those skilled in the art, such as a laser source, a flash or a xenon lamp.

The measurements of the emission, intensity and lifetime of the different fluorescent compounds used in the method of the invention are carried out by means of the FRET signals using conventional methods well known to those skilled in the art. The appropriate readers for detecting the time-resolved FRET signal according to the method of the invention are of the RUBYstar or PHERAstar type from BMG Labtech, or other readers compatible with time-resolved measurements, such as ULTRA, ULTRA Evolution or GENios Pro from TECAN or Analyst from Molecular Devices. The ratio between the fluorescence of the first fluorescent compound and the fluorescence of the second fluorescent compound or other fluorescent compounds (in the case of a multiplex analysis) is calculated by a method known to those skilled in the art which is described in particular in EP 569 496 B 1.

The fluorophores used to label the biomolecules are TR-FRET partner fluorescent compounds. According to the invention, "TR-FRET partner fluorescent compounds" are understood as meaning pairs of fluorescent compounds whose fluorescence spectra partially overlap and in which the donor is a long-lived fluorescent compound and the acceptor is a shorter-lived fluorescent compound than the donor. Those skilled in the art are capable of selecting pairs of TR-FRET partner fluorescent compounds for carrying out the method according to the invention.

In an alternative mode of carrying out the method according to the invention, and in the case where it is desired to study conformational changes of a biomolecule in the cell, the two fluorescent compounds are used to label one and the same biomolecule.

In one practical variant, the method according to the invention comprises additional steps for labeling biomolecules with other fluorescent compounds, making it possible to study more complex biological phenomena. In this case the system will still comprise a first long-lived donor fluorescent compound, together with several other TR-FRET partner acceptor fluorescent compounds, making it possible to measure several interactions, translocations or conformational changes in one and the same cell.

Biomolecules

"Biomolecules" are understood as meaning molecules present in a living organism, and particularly molecules constituting the structure of an organism and those involved in the production and transformation of energy or in the transmission of biological signals. This definition encompasses nucleic acids, proteins, sugars, lipids, peptides, oligonucleotides, metabolic intermediates, enzymes, hormones and neurotransmitters.

The biomolecules which can be studied by means of the method according to the invention are all types of molecules that are expressed in living cells in culture by virtue of heterologous expression techniques known to those skilled in the art. These biomolecules can be e.g. any proteins, any lipids, sugars or oligonucleotides artificially produced by living cells, e.g. membrane receptors such as tyrosine kinase receptors and 7-domain transmembrane receptors coupled with G proteins and subunits of heterotrimeric G proteins, non-membrane receptors such as hormone receptors, ion channels, transporters present on the membrane (aquarines, sodium transporters, bicarbonate ($HCO_3$) transporters), ion pumps (sodium/potassium pump), signal transduction proteins such as monomeric G proteins, enzymes such as kinases, phosphatases, transglutaminases, hydrolases, halogenases, lipases, transferases and metabolic enzymes, scaffold proteins such as SOS, GRB, IRS and HSP, lipid binding proteins, proteins containing PH or FYVE domains which are associated with the membrane by lipid anchoring of the N-myristoylation, S-palmitoylation, S-prenylation or geranylgeranylation type, proteins associated with receptors coupled with G proteins (monomeric or trimeric), such as GEFs, GAPs and RGS, subunits of heterotrimeric G proteins and 7-domain transmembrane receptors coupled with G proteins, adaptor proteins such as proteins containing SH2 or SH3 domains, transcription factors such as c-fos, c-jun and CREB, mitochondrial proteins (such as respiratory chain proteins, cytochromes C, caspases, PBR, etc.), phospholipids, nuclear proteins such as DNA polymerases, helicases and topoisomerases, proteins of the "death" receptor family, such as FAS, apoptosis proteins such as those of the bcl-2 family, and cell cycle proteins such as cdk and cyclines.

Living Cells

The living cells used in the present invention are all types of living cells cultured by techniques known to those skilled in the art, e.g. prokaryotic cells (bacteria), yeasts, immortalized eukaryotic cell lines, insect cells, and primary cultures such as those originating from mammalian blood, tissues or organs. It is important to emphasize that the method of the invention makes it possible to work on living cells and to preserve the integrity of the intracellular biochemical mechanisms: the cell membranes are not permeabilized as in the case of other methods of the prior art, and the cells do not need to be bound.

The interactions between molecules which can be revealed by the method according to the invention are numerous and varied and depend on the nature of the biomolecules used in said method. These interactions can be e.g. the interactions between the androgen receptor and androgen which induce a translocation of the cytoplasm receptor to the cell nucleus, of PKC-γ, which undergoes a translocation, after stimulation of the cytoplasm, to the lipids making up the cell plasma membrane, of the calcineurin complex, which requires binding with calmodulin in order to be active, of p65/p50, etc.

The conformational changes of biomolecules within the living cell itself can take place under certain stimulation circumstances, it being possible for these modifications to be e.g. beta-arrestin, EPAC (cAMP binding proteins), small monomeric G protein exchange factors (GEFs), ion channels such as $K^+$ channels dependent on the rapid inactivation potential, etc.

Fluorescent Compounds

Several fluorescent compounds, also called fluorophores, are used in the method of the invention, the first of these compounds having a long fluorescence lifetime and the others generally having short fluorescence lifetimes. In all cases the fluorescent compounds are TR-FRET partners.

The long-lived fluorescent compounds that are particularly appropriate for the purposes of the invention preferably have a lifetime equal to or greater than 100 nanoseconds.

More precisely, these appropriate fluorescent compounds are rare earth complexes such as cryptates and chelates, particularly cryptates containing one or more pyridine units. Such rare earth cryptates are described e.g. in patents EP 180 492, EP 321 353, EP 601 113 and WO 01/96 877. Cryptates of terbium ($Tb^{3+}$) and europium ($Eu^{3+}$) are particularly appropriate for the purposes of the present invention. Rare earth chelates are described especially in patents U.S. Pat. Nos. 4,761,481, 5,032,677, 5,055,578, 5,106,957, 5,116,989, 4,761,481, 4,801,722, 4,794,191, 4,637,988, 4,670,572, 4,837,169 and 4,859,777. Other chelates are made up of a nonadentate ligand such as terpyridine (EP 403 593, U.S. Pat. Nos. 5,324,825, 5,202,423, 5,316,909).

One particular example of a rare earth chelate that is suitable for the purposes of the invention is the chelate of the formula:

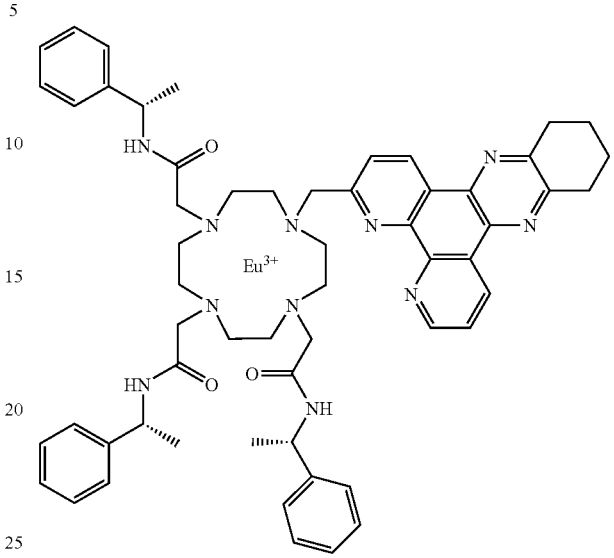

The synthesis of this compound, which can be used as a donor member of a pair of FRET partners, is described by Poole R. et al. in Org. Biomol. Chem., 2005, 3, 1013-1024 "Synthesis and characterisation of highly emissive and kinetically stable lanthanide complexes suitable for usage in cellulo". Example 6 below shows that this type of compound can be used to quantify time-resolved signals in the cell.

The short-lived fluorescent compounds can be selected from fluorescent proteins such as the green fluorescent protein (GFP) and its derivatives (especially CFP, YFP), and fluorescent compounds with a lifetime of less than 100 nanoseconds, such as cyanins, rhodamines, fluoresceins, squarenes and fluorescent molecules known as BODIPYs (difluoroboradiazaindacenes), compounds known as AlexaFluor, fluorescent proteins extracted from corals, phycobiliproteins such as B-phycoerythrin, R-phycoerythrin, C-phycocyanin and allophycocyanins, particularly those known as XL665, and quantum dots. Other appropriate fluorescent compounds are described in patent application FR 2 840 611 and comprise a fluorophore coupled with an oligonucleotide.

Labeling of the Biological Molecules with the Fluorescent Compounds

The different methods of labeling the biomolecules with fluorescent compounds are described in detail below.

1) Generation of a fusion protein between the biomolecule(s) of interest and a protein possessing intrinsic fluorescence properties, such as proteins of the GFP family. The expression of such fusion proteins employs techniques of molecular biology that are well known to those skilled in the art and consist e.g. in stably or transitorily transfecting, into the living cell, expression vectors, such as plasmids, whose DNA codes for the fusion protein.

2) Generation of a fusion protein between the biomolecule(s) of interest and a protein with suicidal enzymatic activity, e.g. the proteins SnapTag (Covalys) or HaloTag (Promega), (hereinafter, "SnapTag" and "HaloTag," respectively) which covalently and irreversibly transfer the fluorescent compound onto the biomolecule(s) of interest. The fluorescent compound in this case is covalently bonded to the substrate of the suicide enzyme and is introduced into the extracellular medium. The techniques described below make it possible to cause the fluorescent compound/substrate conjugates, which would not naturally be lipophilic, to cross the cell membrane.

Suicide enzymes are proteins whose enzymatic activity is modified by specific mutations which give them the capacity to bind a substrate rapidly and covalently. These enzymes are called suicide enzymes because they can each bind only one fluorescent molecule, the activity of the enzyme being blocked by the binding of the substrate. At the present time, two known families of suicide enzymes allow this type of labeling:

- the mutant of an alkylguanine-DNA alkyltransferase (or SnapTag, marketed by Covalys) (cf. Klepper A. et al. (2003) in Nature Biotechnology, vol. 21, p. 86, and WO 02/083937 A2), for which one of the substrates is benzylguanine;
- the mutant of a dehalogenase (HaloTag, marketed by Promega), which also generates an enzymatic reaction of the suicide type (cf. WO 04/072232 A2) and for which some of the substrates are compounds of the chloroalkane family.

In both these cases the substrate which will be incorporated by these suicide enzymes will first have to be labeled with a fluorescent organic compound.

3) Generation of a fusion protein between the biomolecule(s) of interest and a sequence that acquires a protein splicing activity after binding with a complementary sequence previously labeled with the fluorescent molecule(s) of interest, thereby covalently and irreversibly transferring the fluorescent compound by means of a peptide linkage onto the target biomolecule(s), such as the sequence coding for the intein domain of Ssp DnaE.

This approach exploits a biological post-transductional maturation process called protein splicing. This process catalyzes a series of chemical reactions with the ultimate aim of removing a domain, called intein, present in a precursor protein, and binding, by means of a peptide linkage, the two domains located on either side of the intein domain. Protein trans-splicing requires two halves of complementary intein domain. The first half is fused with the target protein and the second half with the fluorescent molecule. This method is described by Muir T. W. et al. (2003) J. Am. Chem. Soc. 2003, 125, 7180-7181. The techniques described below make it possible to cause the "fluorescent compound/intein" conjugates, which would not naturally be lipophilic, to cross the cell membrane.

4) Generation of a fusion protein between the biomolecule(s) to be studied and a peptide sequence or a member of a pair of binding partners possessing characteristics of specific recognition and high-affinity binding with a substrate previously labeled with the fluorescent molecule(s) of interest, such as:

- The sequences cysteine-cysteine-X-X-cysteine-cysteine (CCXXCC), (SEQ ID NO: 1), which have the property of binding to bi-arsenic compounds. These bi-arsenic compounds can easily be labeled with an organic molecule of the fluorescein or rhodamine type (cf. B.A. Griffin et al.(1998) Science 1998, 281, 269-271, and S.A. Adams et al. (2002) J. Am. Chem. Soc. 2002, 124, 6063-6076, for details of the technology).
- Polyhistidine repetitions bind to metal ions which can be coupled with "quencher" molecules of fluorescent compounds (cf. E. G. Guignet et al. (2004), Nature Biotech. 2004, 22, 440-444).
- The tag BTX (bungarotoxin), made up of a peptide of 13 amino acids that is recognized by bungarotoxin (BTX), can be coupled beforehand with a fluorescent molecule (cf. C. M. McCann et al. (2005), Biotechnique (2005), 38, 945-952).
- The binding sequence of streptavidin (SBP-tag) is a sequence made up of 38 amino acids that has a high affinity for biotin, which can be labeled beforehand with a fluorophore (cf. C. M. McCann et al. (2005), Biotechnique (2005), 38, 945-952).

5) Generation of a fusion protein between the biomolecule(s) to be studied and a peptide sequence recognized by certain enzymes, such as transglutaminases or ligases, which transfer the fluorescent compound, previously bound to the enzyme substrate, onto a specific amino acid of the Tag sequence.

The peptide sequence PKPQQFM (Proline-Lysine-Proline-Glutamine-Glutamine-Phenylalanine-Methionine) (SEQ ID NO: 2) is recognized e.g. by an enzyme called transglutaminase. The transglutaminase transfers the fluorescent organic compound, coupled with its substrate(cadaverin), directly onto the first glutamine residue of the sequence PKPQQFM (SEQ ID NO: 2) (cf. Taki et al. (2004) Protein Engineering, Design Selection, 2004, 17, 119-12). The techniques described below make it possible to cause the fluorescent compound/substrate conjugates, which would not naturally be lipophilic, to cross the cell membrane. The sequence of the *E. coli* enzyme dihydrofolate reductase (eDHFR) specifically binds, with a high affinity, ligands such as trimethoprim onto which fluorescent compounds can be grafted according to the technology known as "ligand link universal labeling technology" from Active Motif.

6) Nucleic sequences can also be specifically recognized by enzymes with transferase activities, enabling them covalently to bind a fluorescent organic molecule, present on a cofactor or a substrate, directly to the specific sequence. Such a process can be illustrated by the specific nucleic sequence 5'-TCGA-3', onto which the methyltransferase Taq1 transfers the fluorescent compound which has previously been grafted onto the cofactor aziridine (cf. Pljevaljcic G. et al. (2004) ChemBioChem, 5, 265-269).

In the method according to the invention, the fluorescent compound/biomolecule labeling is therefore carried out by coupling the fluorescent compound and the biomolecule respectively with the members of pairs selected from the following: a SnapTag substrate/the enzyme SnapTag, a HaloTag substrate/the enzyme HaloTag, an intein part such as the intein of Ssp DnaE/the complementary intein part for reconstituting a functional intein, a bi-arsenic unit/the sequence Cys-Cys-X-X-Cys-Cys (SEQ ID NO: 1), X representing any amino acid, a metal ion/a polyhistidine sequence, biotin/streptavidin, streptavidin/biotin, bungarotoxin/the tag BTX, cadaverin/the protein sequence PKPQQFM (SEQ ID NO: 2), aziridine/the nucleic sequence TCGA.

The above-mentioned labeling techniques sometimes involve causing compounds which are not naturally lipophilic, and which do not naturally enter the cell, to cross the cell membrane. These compounds, or their conjugates with substrates, tags or members of a pair of binding partners such as described above, can be introduced into the cell e.g. by using one of the following techniques:

1). Use of esters which mask the charged groups during passage through the lipid bilayer; these esters fall into the category of compounds called prodrugs and refer to compounds which are rapidly transformed in vivo to give the "parent" compound following hydrolysis under physiological conditions [T. Higuchi and V. Stella in "Pro-drugs as Novel Delivery Systems", vol. 14 of the A.C.S. Symposium Series, American Chemical Society (1975)]. Examples include mainly pivaloyloxymethyl and acetoxymethyl groups as well as glycolic esters [Nielsen and Bundgaard, Int. J. of Pharmacy 39 (1984) 75-85]. When this technique is used, one of these groups is covalently grafted onto the fluorophore.

2). Use of viral peptides covalently grafted onto the fluorophore: some of these peptides actually make it possible to transport the fluorophore across the cell membrane. Examples of such viral peptides which may be mentioned are analogs of "Penetratin" and "transportan" [Langel et al., Bioconj. Chem. (2000), 11, 619-626], polyarginines [Wender et al., Arginine-based molecular transporters. Org. Lett. (2003), 5(19), 3459-3462], or else peptoids, peptide analogs carrying guanidine groups [The design, synthesis, and evaluation of molecules that enable or enhance cellular uptake: peptoid molecular transporters. Wender et al., Proc. Natl. Acad. Sci. USA (2000), 13003-8] or non-hydrolyzable derivatives containing tetraguanidinium units [Fernandez-Carneado J. et al., J. Am. Chem. Soc. 2005, 127, 869-874].

3). Modification of the lipophilicity and polarity of the fluorescent compounds by the addition of side chains containing molecules of cholesterol or vitamin E or aliphatic chains which interact with the cell membranes, following the approach exemplified on oligonucleotides using undecylglycerol or 1,2-di-O-hexadecylglycerol chains [3'-end conjugates of minimally phosphorothioate-protected oligonucleotides with 1-O-hexadecylglycerol: synthesis and anti-ras activity in radiation-resistant cells. Rait et al., Bioconj. Chem. (2000), 11, 153-160].

These modifications are more effective than cationic surfactants (cationic "lipids"), which form supramolecular complexes with nucleic acids and increase endocytosis, but are toxic and damage the cell membranes.

Advantageously, in the method according to the invention, at least one fluorescent compound contains a unit that enables it to cross the plasma membrane, said unit being selected from the following groups: esters such as pivaloyloxymethyl esters, acetoxymethyl esters or glycolic esters; and viral peptides taken over by membrane transporters, such as Penetratin and its analogs, transportan and its analogs, polyarginine groups, peptoids carrying guanidine groups such as oligoguanidinium groups, cholesterol or vitamin E groups, or aliphatic chains such as undecyl or 1,2-di-O-hexadecylglycerol chains.

In one alternative mode of carrying out the method, at least two TR-FRET partner fluorescent compounds contain such units that enable them to cross the plasma membrane.

Advantageously, it is possible to bind the fluorescent compound to the substrate for the suicide enzyme and at the same time to generate on said fluorescent compound a reactive chemical group such as, in particular, an amine or acid group, which subsequently makes it possible to couple with said fluorescent compound a unit that enables it to cross the plasma membrane.

For examples, reference may be made to FIGS. 7 and 8, which illustrate the synthesis of a conjugate between a fluorescent compound, namely the compound DY647 (from DYOMICS), and the substrate for a suicide enzyme (substrate for the enzyme "SnapTag"), namely benzylguanine onto which an amine functional group has been added, and the introduction of a reactive chemical group into said fluorescent compound (this conjugate is hereafter referred to as the "tripod").

Said unit that makes it possible to cross the plasma membrane can subsequently be introduced by covalent bonding via this reactive chemical group.

The tripod with an $NH_2$ group will make it possible to integrate vector systems possessing a COOH group, and the tripod with a COOH group will make it possible to integrate vector systems possessing an $NH_2$ group.

The invention further provides a kit of parts comprising the reagents for carrying out the method of detecting interactions between biomolecules or the translocation or conformational change of biomolecules in living cells according to the invention.

This kit comprises:
a first fluorescent compound and a second fluorescent compound, these compounds being TR-FRET partners and at least one of these compounds containing a unit that enables it to cross the plasma membrane;
living cells comprising said biomolecules;
means of labeling the biomolecules with the fluorescent compounds; and
instructions for studying the phenomena of interactions between biomolecules or the translocation or conformational change of biomolecules in living cells.

The reagents contained in this kit make it possible to label the biomolecules to be studied, present in the living cell, with the TR-FRET partner fluorescent compounds: in practice, this means that the fluorescent compound and the biomolecule are coupled respectively with the members of pairs selected from the following: a SnapTag substrate such as benzylguanine/the enzyme SnapTag, a HaloTag substrate such as a chloroalkane/the enzyme HaloTag, an intein part such as the intein of Ssp DnaE/the complementary intein part for reconstituting a functional intein, a bi-arsenic unit/the sequence Cys-Cys-X-X-Cys-Cys(SEQ ID NO: 1), X representing any amino acid, a metal ion/a polyhistidine sequence, biotin/streptavidin, streptavidin/biotin, bungarotoxin/the tag BTX, cadaverin/the protein sequence PKPQQFM (SEQ ID NO: 2), aziridine/the nucleic sequence TCGA.

At least one of the fluorescent compounds further contains a unit that enables it to cross the plasma membrane, said unit being selected from the following compounds: esters such as pivaloyloxymethyl esters, acetoxymethyl esters or glycolic esters; and viral peptides taken over by membrane transporters, such as Penetratin and its analogs, transportan and its analogs, polyarginine groups, peptoids carrying guanidine groups, cholesterol or vitamin E groups, or aliphatic chains such as undecyl or 1,2-di-O-hexadecylglycerol chains.

The living cells contained in this kit can be genetically modified so as to express biomolecules whose interaction it is desired to study. These modifications employ the conventional techniques of molecular biology that are well known to those skilled in the art, such as the stable or transitory transfection of the cells with plasmids expressing the biomolecules, or fusion proteins comprising the biomolecules of interest.

The TR-FRET partner fluorophores contained in the kit according to the invention are a long-lived fluorescent compound and at least one fluorescent compound selected from the following: fluorescent proteins such as the green fluorescent protein (GFP) and its derivatives (especially CFP, YFP), and fluorescent compounds with a lifetime of less than 100 nanoseconds, such as cyanins, rhodamines, fluoresceins, squarenes and fluorescent molecules known as BODIPYs (difluoroboradiazaindacenes), compounds known as AlexaFluor, fluorescent proteins extracted from corals, and phycobiliproteins such as B-phycoerythrin, R-phycoerythrin, C-phycocyanin and allophycocyanins, particularly those known as XL665.

Preferably, the long-lived fluorescent compound has a lifetime greater than 100 ns; particularly preferably, it is a rare earth chelate or cryptate. In one particular formulation of the kit according to the invention, the rare earth is terbium or europium.

The present invention can now be described in greater detail by means of the following illustrative Examples, which shall not in any case limit the applications of the present invention.

BRIEF DESCRIPTION OF THE DRAWINGS:

The patent or application file contains at least one drawing executed in color. Copies of this patent or patent application publication with color drawing(s) will be provided by the Office upon request and payment of the necessary fee.

EXAMPLE 1

Figure 1:
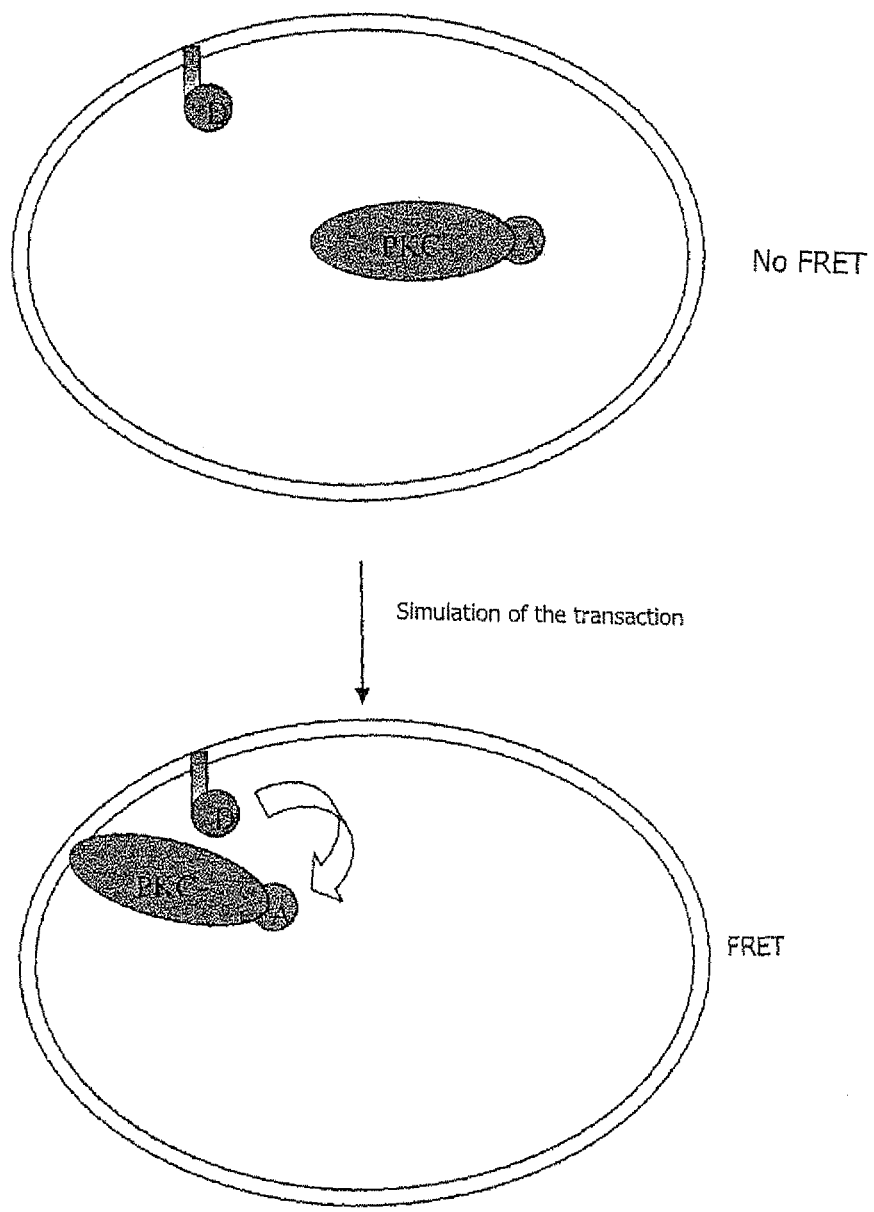
FIG. 1 shows a representative technique for the measurement of the translocation of protein kinase C-gamma (PKC-γ) using FRET.

Measurement of the Translocation of Protein Kinase C-gamma (PKC-γ) (cf. Flow Chart, FIG. 1)

Protein kinases C are proteins belonging to a group of phospholipid-dependent serine/threonine kinases. These proteins play a major role in numerous cell signaling pathways. Physiologically PKC-γ is activated in a calcium-dependent manner by phosphatidylserines (PS) and it binds diacylglycerol (DAG), but PKC-γ can be activated independently of the presence of DAG by tumor-inducing phorbol esters (PMA).

After stimulation, PKC-γ undergoes a translation of the cytoplasm into the plasma membrane, it being possible for this translocation to be measured by means of a fusion protein with GFP after stimulation with PMA (Sakai N. J., Cell Bio. (1997) 139, 1465-1476).

A fusion protein was created between PKC-γ and a suicide enzyme, called HaloTag, in order to label the PKC-γ with an acceptor fluorescent organic compound, and a tool was developed to label the plasma membrane specifically with a donor fluorescent organic compound capable of participating in a FRET with the labeled PKC-γ.

The plasma membrane is specifically labeled with a suicide enzyme, called SnapTag, fused with a sequence Cys-Ala-Ala-X (X being any amino acid) (SEQ ID NO: 3), which is a sequence recognized by the enzymes of post-transductional modification. This sequence will cause the grafting of a farnesyl group in the C-terminal position of the SnapTag enzyme, which has the consequence of targeting and anchoring this enzyme on the inner layer of the plasma membrane. COS-7 cells were transitorily transfected with the two plasmid constructs using lipofectamine 2000 or by electroporation.

24 h or 48 h after the transitory transfection, the cells are incubated for 1 hour with cellular medium containing 5 µM of each substrate specific for the HaloTag and SnapTag enzymes, the substrates each carrying the fluorescent organic molecules forming the FRET.

After 3 washes with medium, the translocation is measured by TR-FRET after induction by different stimulations, e.g. after the addition of 12-myristate 13-acetate phorbol ester (PMA). An increase in the TR-FRET signal correlates with an increase in the translocation process.

Molecules that potentially inhibit the translocation pathway of the PKC-γ can be added to the culture medium in order to test their effects on the stimulation of the translocation.

EXAMPLE 2

Figure 2:
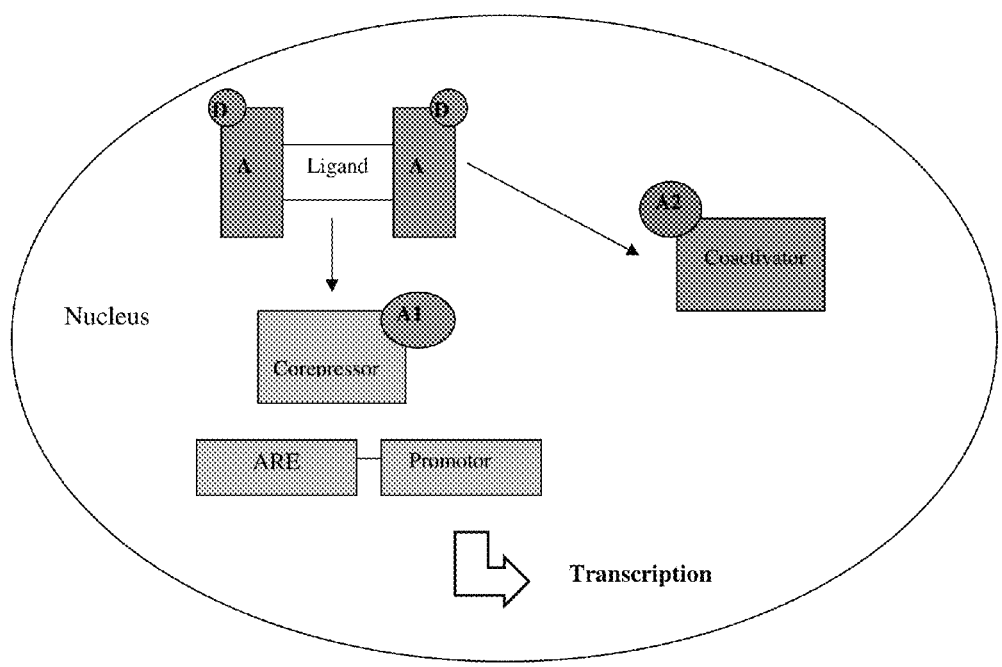
FIG. 2 shows a representative technique for the measurement of androgen receptor/coactivator or androgen receptor/corepressor interactions.

Revealing Androgen Receptor/Coactivator or Androgen Receptor/Corepressor Interactions (cf. Flow Chart, FIG. 2)

Androgens and their functional receptor (AR) are responsible for normal differentiation of the external male phenotype. Cytosolic androgen receptors, in the inactive state, are associated with heat shock proteins. After binding with the ligand, the receptors dimerize and are subjected to a translocation into the nucleus. AR coregulators (coactivators or corepressors) will or will not then interact with the receptor and the result of these interactions will optionally cause the complex to bind to the DNA at a specific sequence (called ARE=androgen receptor responsive element) and thus to regulate the transcription.

The method according to the invention is used to reveal the interactions between a corepressor, a coactivator and an AR. This is done by introducing expression vectors into the cell in order to express the following in the intracellular medium:
- an AR/SnapTag enzyme fusion protein. The SnapTag suicide enzyme allows coupling with a fluorescent compound labeled with a SnapTag substrate.
- an HDAC1/HaloTag fusion protein. HDAC1 (histone acetyltransferase 1) is a corepressor capable of binding to AR. The HaloTag suicide enzyme allows coupling with a fluorescent compound labeled with a HaloTag substrate.
- a p160/intein fragment fusion protein. P160 is a coactivator capable of binding to AR. The intein fragment allows coupling with a fluorescent compound containing the complementary intein fragment by protein trans-splicing.

If the AR is located in the nucleus after stimulation (binding of its ligand), its final effect can be assayed by measuring the TR-FRET signal: the AR is labeled with the donor fluorescent compound and the coactivator and the corepressor are labeled with two acceptor fluorescent compounds that are quite different in their spectral properties and whose emission wavelengths following an energy transfer are respectively 665 and 780 nm.

The measurement of a TR-FRET signal at 665 nm will therefore be representative of the binding of the AR with its coactivator, whereas the measurement of a TR-FRET at 780 nm will be indicative of an AR/corepressor interaction. This test format therefore makes it possible to detect two types of interaction in a single cell test. This multidetection test can be further improved by adding other acceptor fluorescent compounds to reveal other interactions simultaneously.

Figure 3:
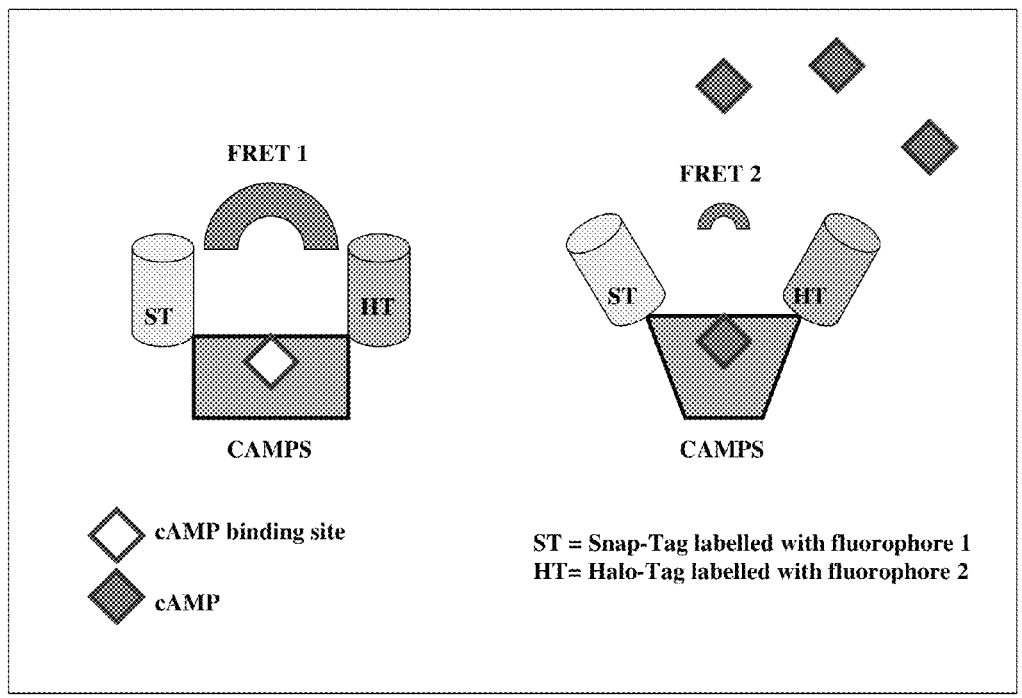
FIG. 3 shows a representative technique for the detection of conformational modifications of a fusion protein comprising a cAMP binding domain.

EXAMPLE 3 cAMP Biosensor: Detection of Conformational Modifications of a Fusion Protein Comprising a cAMP Binding Domain (cf. Flow Chart, FIG. 3)

In this Example the variations in the TR-FRET signal of a pair of donor/acceptor fluorescent compounds is measured by coupling these fluorophores with a cAMP binding domain (e.g. that of the βII regulatory subunit of PKA, or that of cAMP-activated exchange proteins, which are known by the term "CAMPS"). These molecular constructs can be used to quantify, in living cells, the levels of cAMP after pharmacological stimulation of a G protein-coupled receptor (GPCR) (cf. Nikolaev et al., JBC, vol. 279, no. 36, pp 37215-37218, 2004).

The plasmid coding for a fusion protein of the SnapTag/CAMPS/HaloTag type is transfected into HEK cells. 24 hours or 48 hours after transfection, the cells are incubated (1 hour at 37° C.) with the SnapTag and HaloTag substrates, each of which is coupled with a member of a TR-FRET donor/acceptor pair.

When the incubation step is complete, the fluorophores are covalently coupled via suicide reactions of the SnapTag and HaloTag enzymes, and the CAMPS protein is labeled with the pair of fluorophores involved in the TR-FRET.

In the basal state a TR-FRET signal is measured because of the proximity of the fluorophores. After pharmacological stimulation (e.g. stimulation by an agonist of a G protein-coupled receptor expressed in HEK cells), the intracellular concentration of cAMP will increase and the binding of cAMP to CAMPS will cause a conformational change in the latter protein. A decrease in the measured TR-FRET signal is then observed.

This Example shows that the amplitude of the TR-FRET signal correlates directly with the binding of the cAMP to the CAMPS protein.

The same experiment can be performed with a GPCR antagonist, which causes a decrease in the cAMP concentration in the cell and a variation in the conformation of the CAMPS protein, which can be detected by measuring an increase in the TR-FRET signal.

EXAMPLE 4

Figure 4:
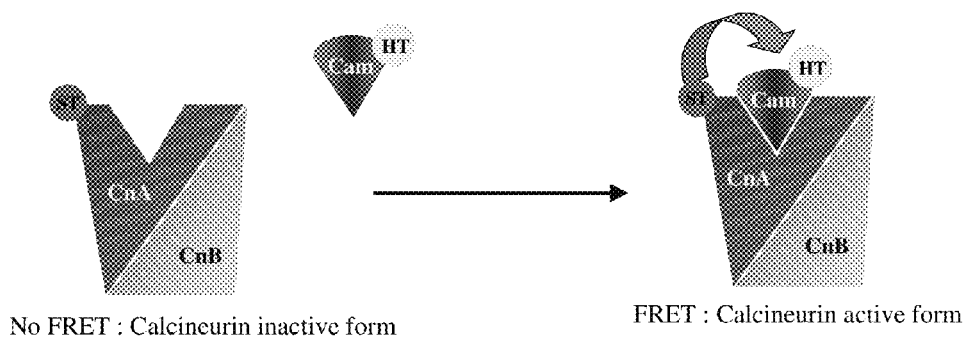
FIG. 4 shows a representative technique for the measurement of the calcineurin/calmodulin interaction.

Measurement of the Calcineurin/Calmodulin Interaction (cf. Flow Chart, FIG. 4)

Calcineurin has a phosphatase activity and plays a fundamental role in the cell signaling pathway that involves the levels of intracellular calcium. Calcineurin is involved in the development of, and adaptation to, stress in mammals by way of two classes of transcription factors: NFAT and MEF2.

Calcineurin is a heterodimer comprising two subunits, calcineurin A (CnA) and calcineurin B (CnB). The enzyme is inactive in its heterodimeric form and the phosphatase activity is stimulated by the formation of a calcineurin/calmodulin complex when the concentration of intracellular calcium increases.

A plasmid coding for a fusion protein comprising the CnA subunit and the HaloTag enzyme and a plasmid coding for a fusion protein comprising calmodulin and the SnapTag enzyme are cotransfected into cells using lipofectamine 2000 or by electroporation. After 24 or 48 hours, the cells are incubated for 1 hour at 37° C. in a medium comprising the substrates for the SnapTag and HaloTag enzymes, each of which is coupled with a member of a pair of fluorophores that is compatible for TR-FRET.

After washing, the cells are stimulated pharmacologically or by a stress (e.g. by cyclosporin A or acidification of the medium). The amplitude of the measured TR-FRET signal increases and correlates with the association of the CnA/CnB heterodimer with calmodulin.

Molecules whose effect on activation of the calcineurin-dependent signaling pathway it is desired to test can be added to the measurement medium before stimulation. This Example shows that the method according to the invention makes it possible to study the calcineurin-dependent signaling pathway in living cells, optionally in the presence of test compounds. This type of test allows the high-throughput screening of candidate compounds that may enable the treatment of pathological conditions involving this signaling pathway.

EXAMPLE 5

Screening of Compounds with Anti-Inflammatory Activity

TNF-alpha is an inflammatory factor that causes several cell responses when it binds to its membrane receptor. One of the responses caused by TNF-alpha in B lymphocytes is activation of the transcription factor NFkB, which controls the production of the light chains of antibodies—a critical step of the immune response. TNF-alpha inhibitors are therefore useful for regulating the immune response and can be used e.g. in the prevention of septic shock or as anti-inflammatory drugs. Such inhibitors of TNF-alpha activity can be discovered by measuring the NFkB activation level, which the present invention is able to do.

Figure 5:
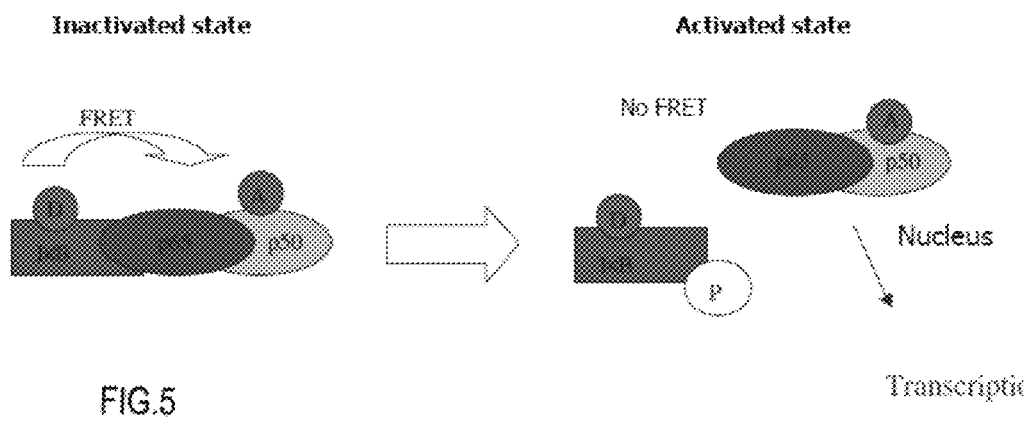
FIG. 5 illustrates the cytosolic retention of NFkB by the cytosolic protein IkB: the NFkB(p65,p50)/IkB complex is retained in the cytosol. An appropriate stimulation (mitogens of T and B cells, lipopolysaccharide and TNF-alpha) causes the phosphorylation of IkB and its degradation and releases NFkB, which can then penetrate the cell nucleus and activate the production of the light chains of antibodies.

FIG. 5 illustrates the cytosolic retention of NFkB by the cytosolic protein IkB: the NFkB(p65, p50)/IkB complex is retained in the cytosol. An appropriate stimulation (mitogens of T and B cells, lipopolysaccharide and TNF-alpha) causes the phosphorylation of IkB and its degradation and releases NFkB, which can then penetrate the cell nucleus and activate the production of the light chains of antibodies.

The method according to the invention is applied by introducing the following constructs into B lymphocytes by the conventional techniques of molecular biology:
- a vector expressing an IkB/SnapTag fusion protein, which may be labeled with a donor fluorescent compound conjugated with the SnapTag substrate; and
- a vector expressing a p50/HaloTag fusion protein, which may be labeled with an acceptor fluorescent compound conjugated with a HaloTag substrate.

Under rest conditions, the NFkB(p65/p50) complex forms a complex with IkB and a TR-FRET signal can be measured. After stimulation of the cells with TNF-alpha, the phosphorylation of IkB and its dissociation from the complex will cause the TR-FRET signal to decrease. The amplitude of this decrease is representative of the degree of activation of the NFkB.

These cells are cultivated in a microwell plate and one of the following treatments is applied to different wells:
- addition of the donor and acceptor fluorescent compounds coupled with the SnapTag and HaloTag substrates, and measurement of the TR-FRET signal (high TR-FRET control well);
- addition of the fluorescent compounds coupled with the SnapTag and HaloTag substrates, stimulation of the cells by adding TNF-alpha, and measurement of the TR-FRET signal (low TR-FRET control well);
- addition of the fluorescent compounds coupled with the SnapTag and HaloTag substrates, addition of a test compound, stimulation of the cells by adding TNF-alpha, and measurement of the TR-FRET signal (test wells).

When the signal of the test wells is similar to that measured in the high TR-FRET control wells, it can be concluded that the test compounds have an inhibitory effect on the TNF-alpha activity. When this value is close to the value measured in the low TR-FRET control wells, it can be concluded that the test compounds have no effect on the action of TNF-alpha.

This Example illustrates the application of the method according to the invention to the screening of drugs and is particularly suitable for so-called high-throughput screening.

EXAMPLE 6

Time-Resolved Microscopy of a Europium Chelate

This Example illustrates the use of a fluorescent compound that is naturally capable of crossing the plasma membrane, and its capacity to emit a time-resolved signal in a cell.

a) Protocol

Cells are inoculated into LABTEK culture chambers [density 80,000 c/ml], cultured for 24 hours and then washed with culture medium.

The europium chelate of the formula below is added to the culture medium (concentration 20 µM) and the cells are incubated for 24 hours at 37° C.

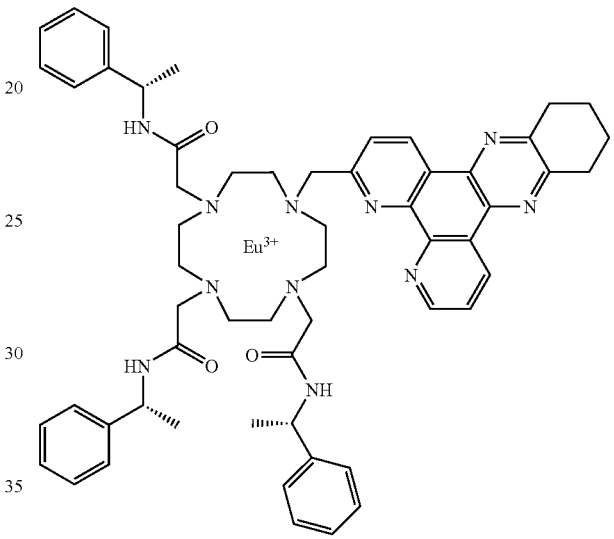

After washing with culture medium, Hoechst dye 33342 [concentration 2 µg/ml; supplier's reference: Sigma Aldrich B2261] is added to the culture chambers, which are then incubated for 15 min in the dark at room temperature. This dye has the property of specifically labeling the cell nuclei.

The culture chambers are washed again with culture medium prior to the acquisition of images by microscopy, in "time-resolved" mode, using the following equipment: an Axiovert 200M microscope (Zeiss), a UV excitation source: a pulsed nitrogen laser (Spectra Physics), and a PI-Max CCD (charge coupled device) intensified camera (Roper Scientific), with the following parameters:
- Reading time 2 milliseconds: the camera detects for 2 milliseconds to recover the whole signal from the chelate;
- Delay 100 microseconds: delay imposed in order to eliminate the parasitic fluorescence before picking up the time-resolved signal;
- Number of cycles per reading: the signal is acquired over 30 exposures during the 2 milliseconds, and then compiled.

b) Results

Figure 6:
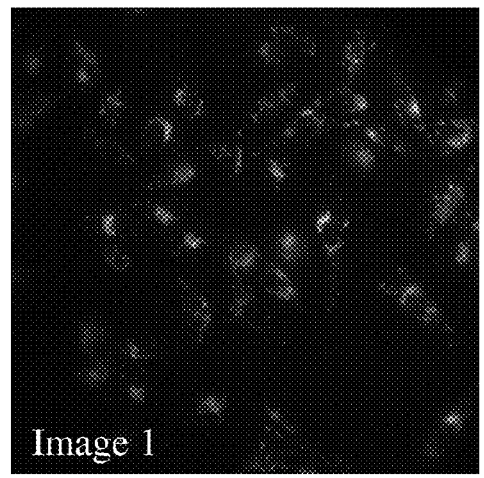
FIG. 6 illustrates the use of a fluorescent compound that is naturally capable of crossing the plasma membrane, and its capacity to emit a time-resolved signal in a cell. The transmission image (image 3) provides assurance of the integrity of the cells and the density of the cellular mat. The Hoechst image (image 2) makes it possible to locate the cell nuclei. The negative control (image 5) shows the signal obtained in time-resolved detection mode in the absence of fluorescent compound. The image obtained with the donor fluorescent compound tested at a concentration of 20µM (image 1) makes it possible to reveal an intracellular location of the FRET donor compound. The superimposition of images (2) and (1) shows that the fluorescence is located in the cell.
Figure 6:
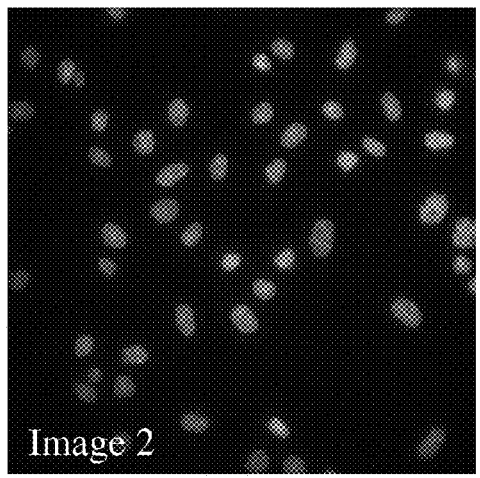
Figure 6:
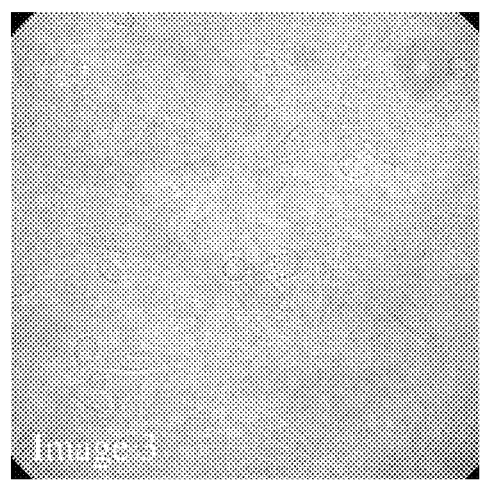
Figure 6:
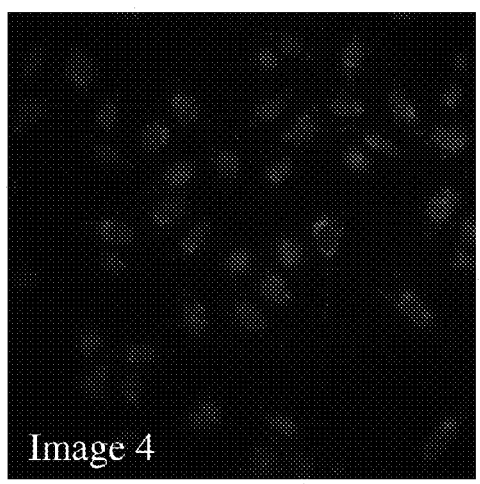
Figure 6:
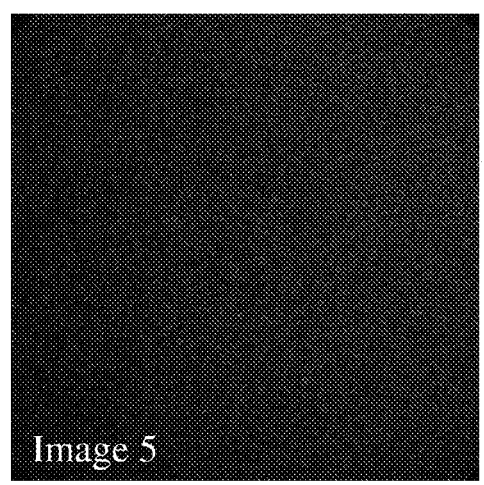

The images obtained are shown in FIG. 6.

The transmission image (image 3) provides assurance of the integrity of the cells and the density of the cellular mat. The Hoechst image (image 2) makes it possible to locate the cell nuclei. The negative control (image 5) shows the signal obtained in time-resolved detection mode in the absence of fluorescent compound.

The image obtained with the donor fluorescent compound tested at a concentration of 20 μM (image 1) makes it possible to reveal an intracellular location of the FRET donor compound. The superimposition of images (2) and (1) shows that the fluorescence is located in the cell. This type of time-resolved measurement can be quantified by designating regions of interest on signal and noise zones and by subtracting the mean value of the noise from the value of the measured signal.

This Example shows that a rare earth chelate capable of crossing the plasma membrane can be used to carry out the invention, and that the signal emitted by such a compound can be measured by time-resolved microscopy.

EXAMPLE 7

Synthesis of a Fluorescent Conjugate Containing a Polyarginine Unit and a Benzylguanine Group, Microscopic Data a) Synthesis of BG-DY647 and Dy647-R9-BG ("R9" disclosed as SEQ ID NO: 7)

Figure 9:
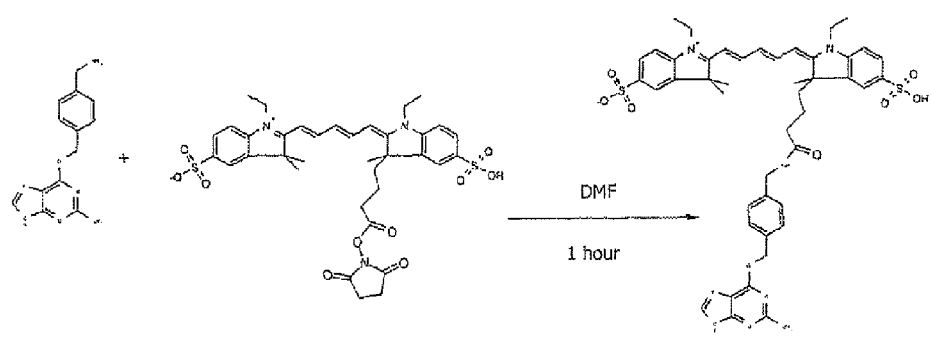
FIG. 9 describes the synthesis scheme for a conjugate comprising the benzylguanine BG (substrate for the SnapTag enzyme), covalently bonded to the fluorescent compound DY647.

FIG. 9 describes the synthesis scheme for a conjugate comprising the benzylguanine BG (substrate for the SnapTag enzyme), covalently bonded to the fluorescent compound DY647.

Figure 10:
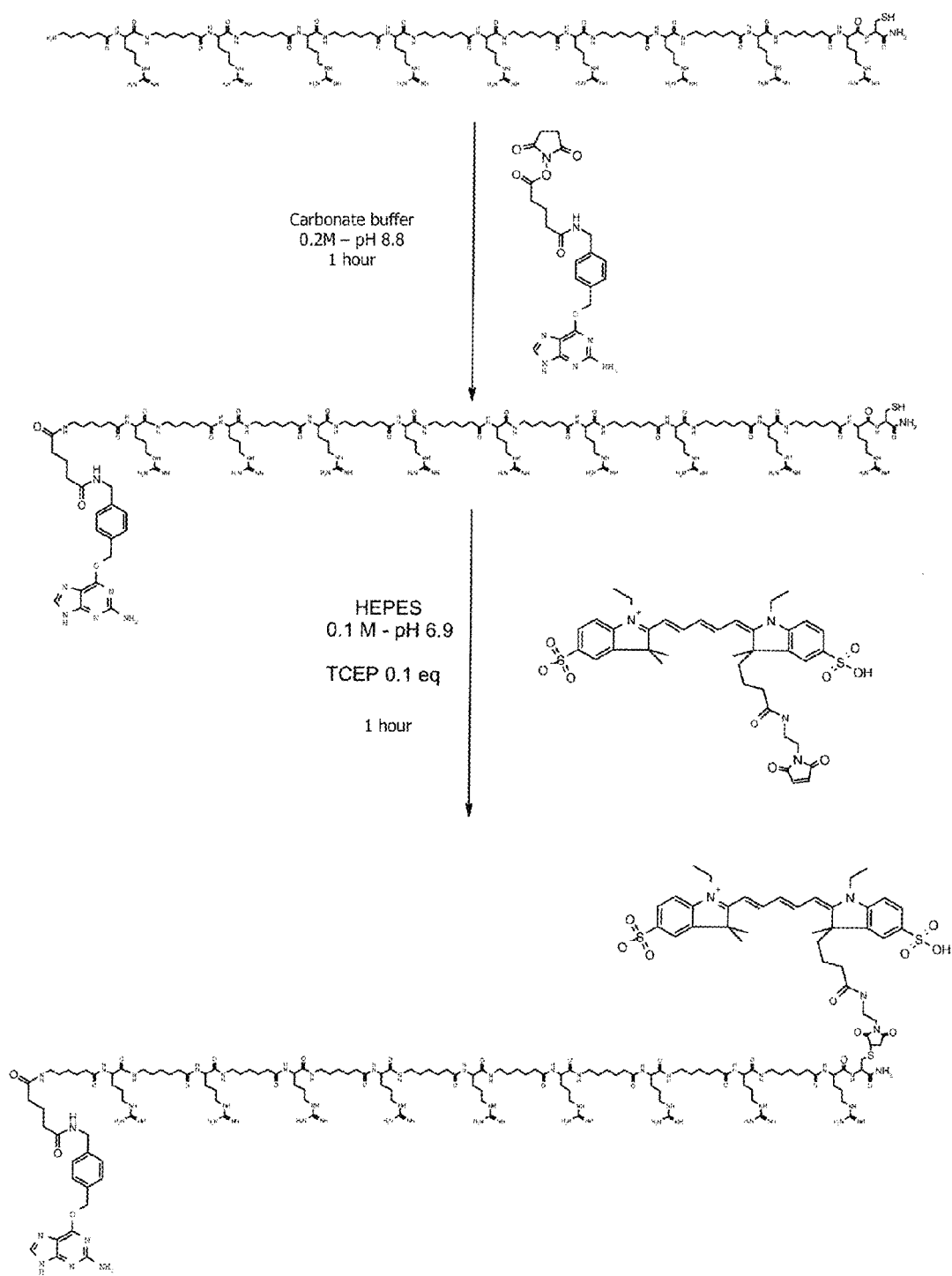
FIG. 10 shows the synthesis scheme for a conjugate comprising a sequence of 9 arginines (R9) (SEQ ID NO: 7), onto which the fluorophore DY647, on the one hand, and the benzylguanine BG, on the other, are grafted.

FIG. 10 shows the synthesis scheme for a conjugate comprising a sequence of 9 arginines (R9) ("R9" disclosed as SEQ ID NO: 7), onto which the fluorophore DY647, on the one hand, and the benzylguanine BG, on the other, are grafted.

b) Microscopic Analysis

CHO cells are cultivated at 37° C., under a controlled atmosphere containing 5% of $CO_2$, in F-12 HAM medium (Invitrogen)+10% of fetal calf serum (FCS) previously inactivated for 20 min at 60° C.

On the day before the experiment, the cells are dissociated and inoculated into LABTEK culture chambers (Nunc) at a density of 75,000 cells/well.

On the day of the experiment, the test compounds (BG-DY647 or Dy647-R9-BG ("R9" disclosed as SEQ ID NO: 7)) are prepared in culture medium at a concentration of 5 μM and brought into contact with the cells for one hour.

After incubation, 3 washes are carried out with culture medium.

Before microscopic analysis, a nuclear staining is carried out with Hoechst dye.

The microscopic analysis is performed with the aid of an Axiovert 200M epifluorescence microscope (Zeiss), a 40× lens, a UV excitation source: a pulsed nitrogen laser (Spectra Physics), and a CoolSNAP CCD camera (Photometrics).

Figure 11:
FIG. 11 shows the images obtained with either the conjugate BG-DY647 or the conjugate DY647-R9-BG ("R9" disclosed as SEQ ID NO: 7).

FIG. 11 shows the images obtained with either the conjugate BG-DY647 or the conjugate DY647-R9-BG ("R9" disclosed as SEQ ID NO: 7). It is seen that the conjugate DY647-R9-BG ("R9" disclosed as SEQ ID NO: 7) is located in the cells, whereas the conjugate BG-DY647 remains in solution in the culture medium. A compound such as DY647-R9-BG ("R9" disclosed as SEQ ID NO: 7) can therefore be used in the method according to the invention, especially as an acceptor conjugate that is capable of crossing the plasma membrane in order to label an intracellular protein comprising the SnapTag enzyme.

EXAMPLE 8

Comparative Example of the Effect of a Polyarginine or Oligoguanidinium Modification on the Entry of a Fluorophore into Cells in Culture, Fluorescence Reader Data a) Protocol CHO cells are cultivated at 37° C., under a controlled atmosphere containing 5% of $CO_2$, in F-12 HAM medium (Invitrogen)+10% of fetal calf serum (FCS) previously inactivated for 20 min at 60° C.

On the day before the experiment, CHO-M1 cells are inoculated into a 96-well plate at a density of 10,000 cells per well.

On the day of the experiment, the culture medium is aspirated and replaced with the test compounds at a concentration of 2.5 μM or 5 μM in KREBS buffer (Sigma). After 1 hour of incubation, the wells are washed with a KREBS buffer+ 0.05% Tween 20. The cells are then lyzed in a PBS buffer+ 0.1% Triton X100. The fluorescence is measured on an Analyst AD reader (LJL, Molecular Devices) with the filters and the dichroic appropriate for the spectral specificities of the compound to be detected.

Example for a compound carrying a fluorescein:
Excitation filter: pass-band 485/22 nm
Dichroic: high-pass 505 nm
Emission filter: pass-band 535/35 nm
Example for a compound carrying a rare earth complex:
Excitation filter: pass-band 330/80 nm
Dichroic: BBUV
Emission filter: pass-band 620/10 nm b) Results 4 compounds were tested under these conditions:
fluorescein, which is naturally capable of crossing the plasma membrane, and carboxyfluorescein, which is not naturally capable of crossing the plasma membrane, as controls;
the derivative R7-fluorescein ("R7" disclosed as SEQ ID NO: 8) of the formula below:

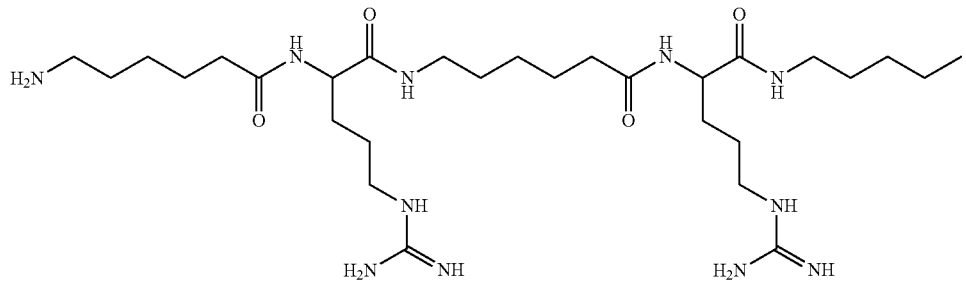

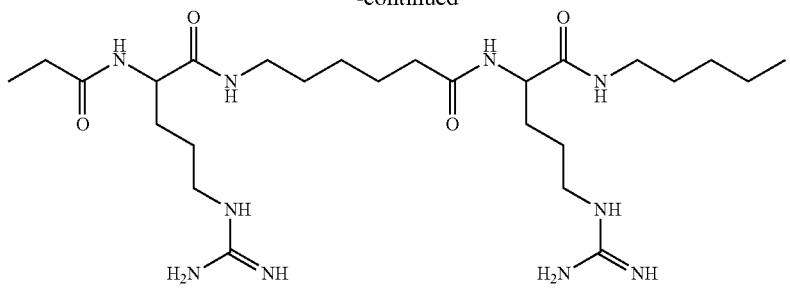

Figure 12:
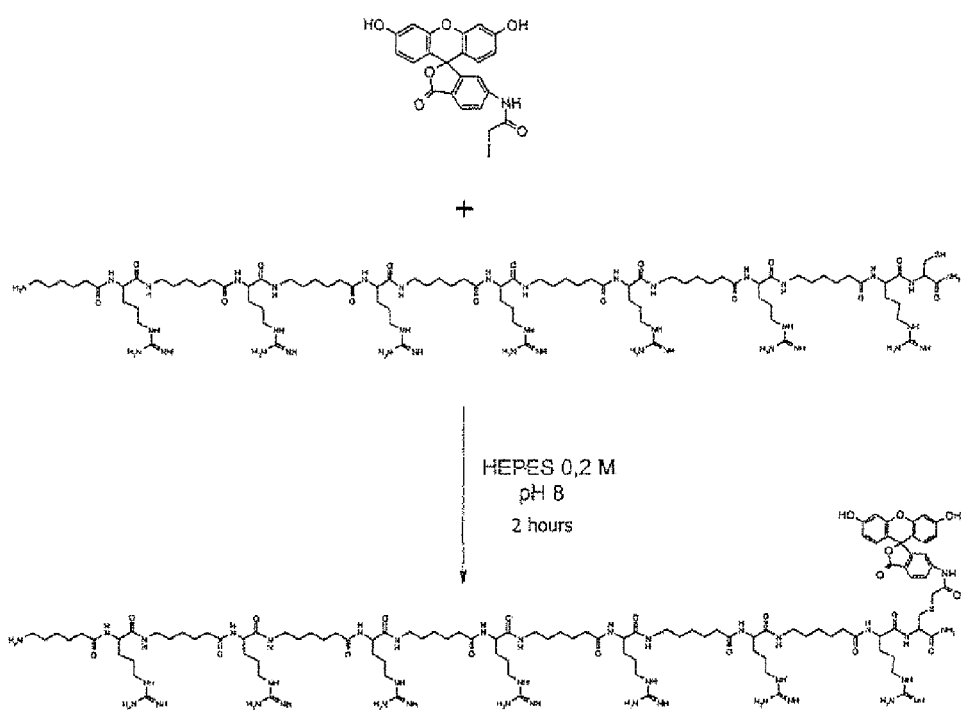
FIG. 12 shows a synthesis scheme for the manufacture of R7-fluorescein ("R7" disclosed as SEQ ID NO: 8) derivative as shown. The compound is synthesized by grafting a polyarginine sequence containing 7 arginine units (SEQ ID NO: 8) onto the fluorescein structure.

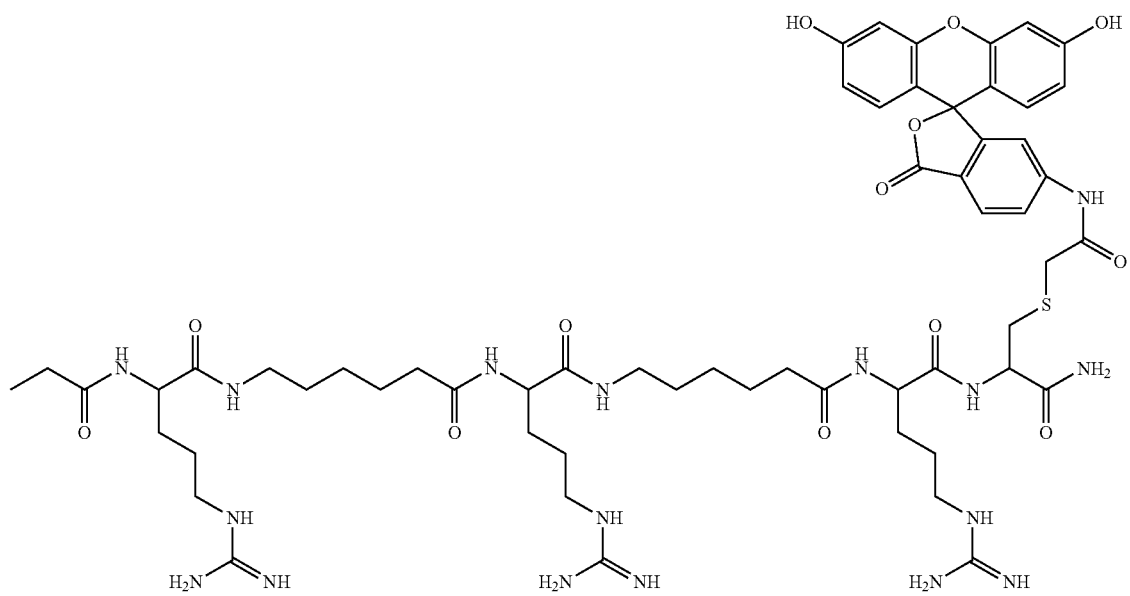

which is obtained by grafting a polyarginine sequence containing 7 arginine units (SEQ ID NO: 8) onto the fluorescein structure according to the synthesis scheme described in FIG. 12;

the derivative tetraguanidinium-fluorescein: a tetraguanidinium sequence (such as described by Fernandez-Carneado J. et al., J. Am. Chem. Soc. 2005, 127, 869-874) was grafted onto the carboxyfluorescein structure:

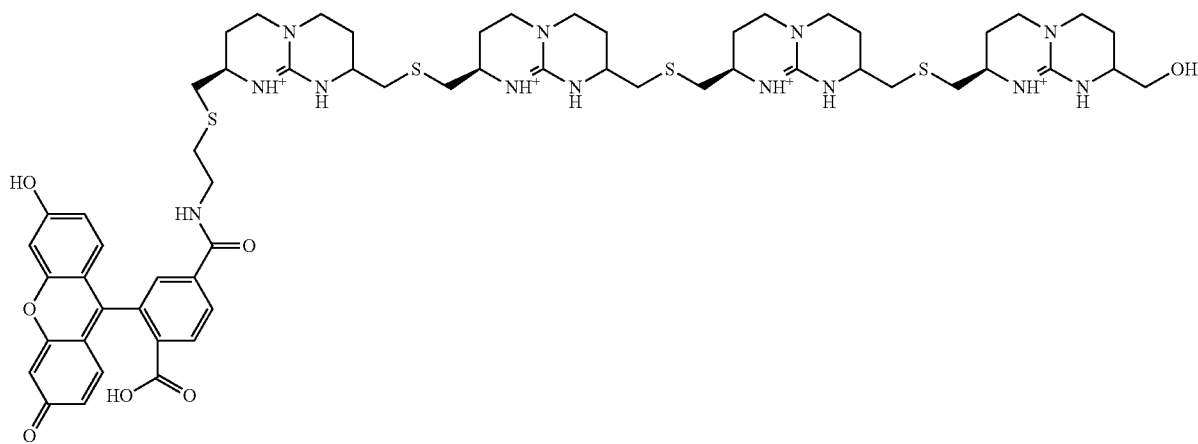 [SMILES: O=C(NCCSC[C@H]1CCN2CCC(CSC[C@H]3CCN4CCC(CSC[C@H]5CCN6CCC(CSC[C@H]7CCN8CCC(CO)NC8=[NH+]7)NC6=[NH+]5)NC4=[NH+]3)NC2=[NH+]1)c1ccc(C(=O)O)c(-c2c3ccc(=O)cc-3oc3cc(O)ccc23)c1]

Figure 13:
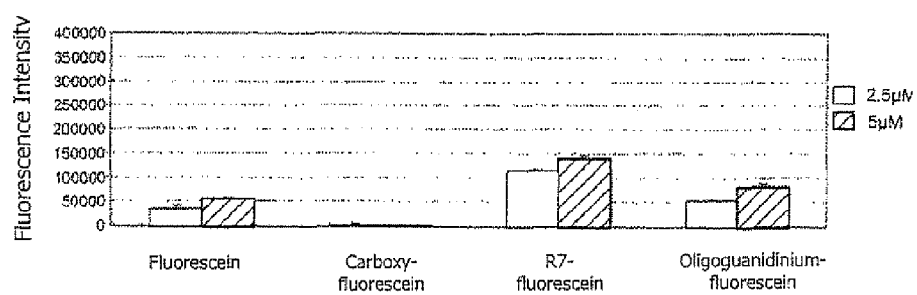
FIG. 13 shows the results of a FRET assay using fluorescein, carboxy-fluorescein, R7fluorescein ("R7" disclosed as SEQ ID NO: 8) and oligoguanidinium-fluorescein. The results indicate that the polyarginine and tetraguanidinium sequences can be used to cause one of the FRET partners to enter the cell, and can therefore be used as units for allowing one of the FRET partners to cross the cell membrane.

The fluorescence intensity measured for each of the compounds (FIG. 13) according to the above protocol shows that the polyarginine and tetraguanidinium sequences can be used to cause one of the FRET partners to enter the cell, and can therefore be used as units for allowing one of the FRET partners to cross the cell membrane.

EXAMPLE 9

Example of Constitutive Intracellular TR-FRET (HaloTag/SnapTag Chameleon)

The method according to the invention is used to reveal a FRET signal in a living cell. This is done by introducing an expression vector into the cell in order to express, in the intracellular medium, a fusion protein composed of SnapTag and HaloTag. The SnapTag suicide enzyme allows coupling with a fluorescent compound labeled with a SnapTag substrate (benzylguanine). The HaloTag suicide enzyme allows coupling with a fluorescent compound labeled with a HaloTag substrate (a chloroalkane).

Obtaining the plasmid construct for the cellular expression of a SnapTag/HaloTag fusion protein:

Plasmid pHT2 carrying the HaloTag sequence originates from Promega.

Plasmid pSem-S1-ST26m carrying the SnapTag sequence originates from Covalys.

The cassette corresponding to the coding sequence of HaloTag is isolated from plasmid pHT2 by enzymatic digestion with EcoRV-NotI (Biolabs) and transferred onto plasmid pCDNA3.1 (Invitrogen) which has previously been digested with the same enzymes.

Ligation is effected with T4 ligase (Invitrogen). Chemocompetent bacteria called Turbo cells (GenetherapySystem) are transformed with the ligation product. The transformed bacteria are plated on LB-agar medium (Sigma)+0.1 mg/ml ampicillin (Eurogentec) to allow selection of the bacteria that possess plasmid pCDNA3.1 HaloTag.

The plasmid DNA is obtained by purification on columns (QIAGEN). The integrity of the sequence is verified by sequencing.

The cassette corresponding to the coding sequence of SnapTag is isolated from pSEM-S1-ST26m by enzymatic digestion with ClaI-XhoI (Biolabs) and transferred onto plasmid pBluescriptKS (Stratagene) which has previously been digested with the same enzymes.

Ligation is effected with T4 ligase (Invitrogen). Chemocompetent bacteria called Turbo cells (GenetherapySystem) are transformed with the ligation product. The transformed bacteria are plated on LB-agar medium (Sigma)+0.1 mg/ml ampicillin (Eurogentec) to allow selection of the bacteria that possess plasmid pBluescriptKS-ST26m. The plasmid DNA is obtained by purification on columns (QIAGEN). The integrity of the sequence is verified by sequencing.

The plasmid that makes it possible to obtain the coding sequence of the SnapTag/HaloTag fusion protein is obtained by transferring the cassette corresponding to the SnapTag sequence, isolated by digestion of plasmid pBluescriptKS-ST26m with XbaI-KpneI (Biolabs), onto plasmid pCDNA3.1 HaloTag which has previously been digested with NheI-KpneI.

The plasmid DNA corresponding to plasmid pBluescriptKS-ST26m-HaloTag is obtained by purification on columns (QIAGEN). The integrity of the sequence is verified by sequencing.

Cos-7 cells are transitorily transfected with plasmid construct pBluescriptKS-ST26m-HaloTag using lipofectamine 2000 or by electroporation in a 96-well plate.

Figure 7:
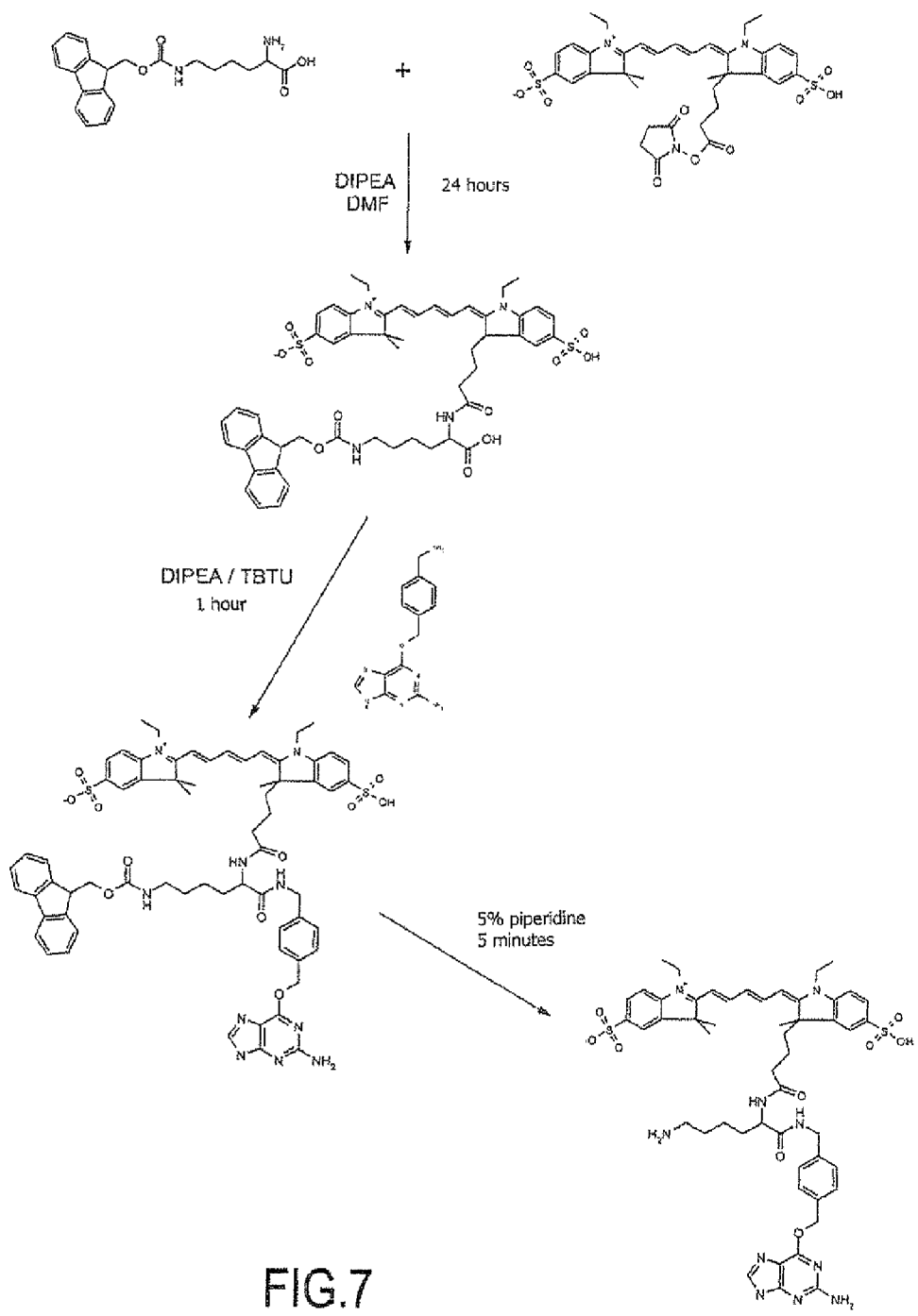
FIG. 7 and FIG. 8, independently, illustrate reaction schemes that are employable in the manufacture of conjugates of the instant application. The conjugates comprise a fluorescent compound, namely the compound DY647 (from DYOMICS), and the substrate for a suicide enzyme (substrate for the enzyme "SnapTag"), namely benzylguanine. A reactive chemical group may be introduced into the fluorescent compound (this conjugate is referred to as the "tripod"). A unit that makes it possible to cross the plasma membrane can subsequently be introduced by covalent bonding via this reactive chemical group. The tripod with an NH2 group will make it possible to integrate vector systems possessing a COOH group, and the tripod with a COOH group will make it possible to integrate vector systems possessing an NH2 group.
Figure 8:
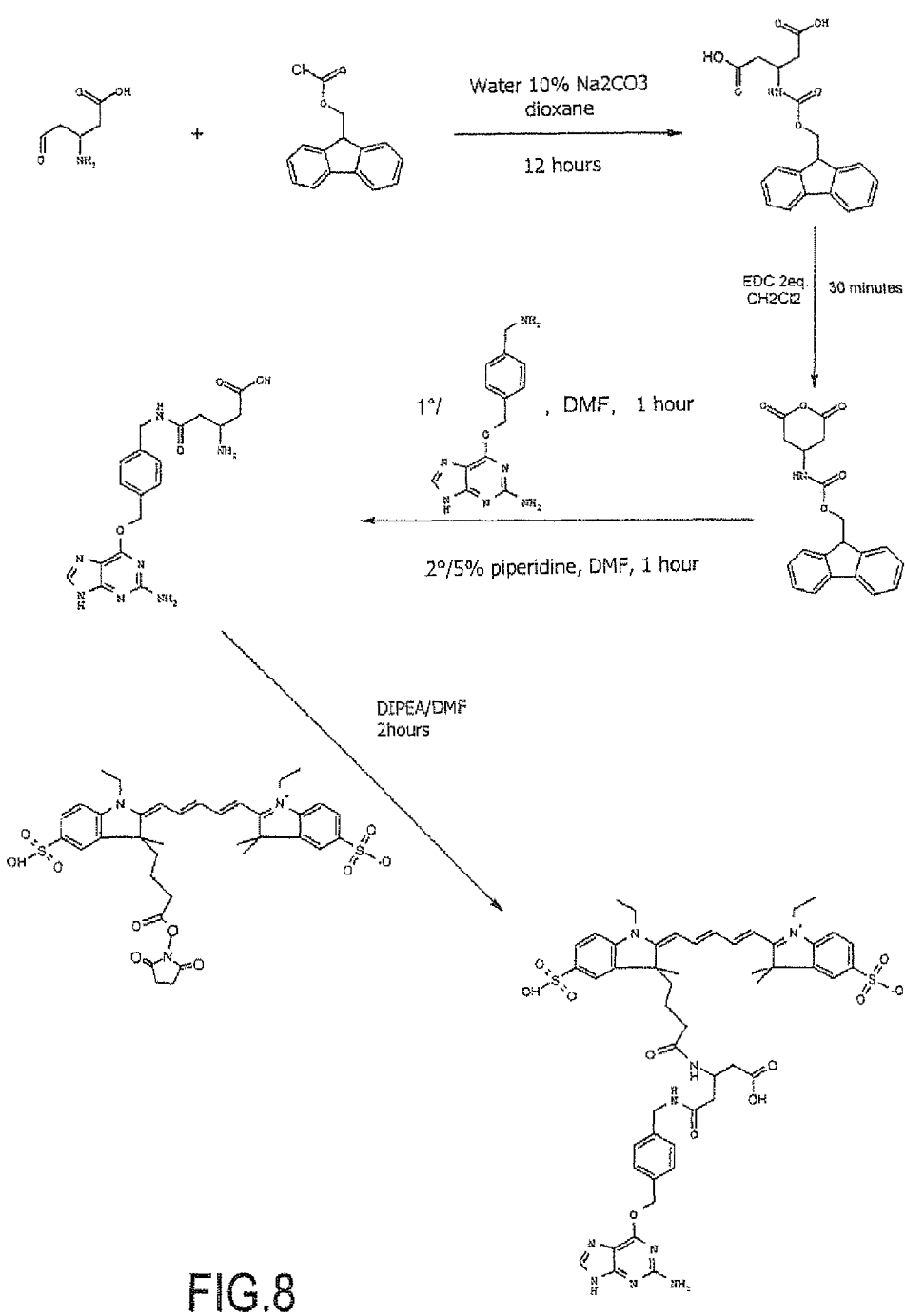

24 h or 48 h after transitory transfection, the COS-7 cells are incubated for 1 hour with cellular medium containing 5 µM of each substrate specific for the HaloTag and SnapTag enzymes, each of the substrates being covalently bonded to a member of a pair of FRET partners and to a unit that enables it to cross the plasma membrane (manufactured e.g. according to the scheme of FIG. 7 or 8).

After 3 washes with KREBS+0.05% Tween 20, a FRET signal is measured on a RubyStar reader (BMG), showing that the method according to the invention can be used to measure a FRET signal generated inside living cells.

EXAMPLE 10

Example of Induced Intracellular TR-FRET (FRB/FKBP)

Model Used:

Here the method according to the invention is applied to revealing the interaction of the intracellular protein FKBP12 and the FRB domain of the protein FRAP when rapamycin is added to the culture medium.

FKBP12 is a 12 kDa protein belonging to the immunophilin family. The binding of rapamycin to FKBP12 renders the protein cytosoluble by dissociating FKBP from these partners.

The protein FRAP (or mTOR) contains the FRB domain: this domain is made up of 99 Amino acids (corresponding to the sequence of mTOR E2015-Q2114).

Figure 14:
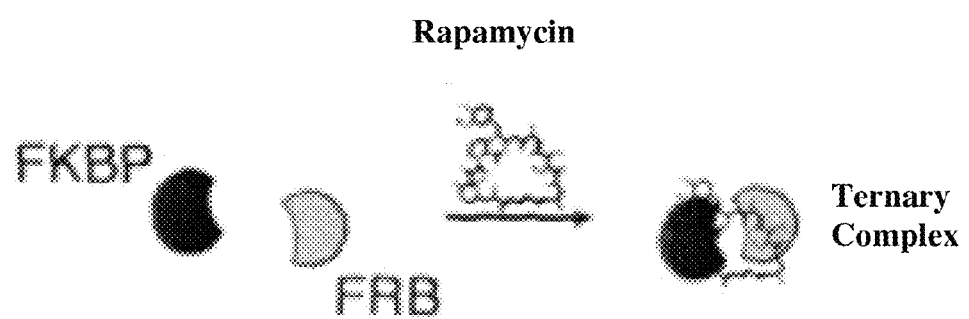
FIG. 14 shows binding of rapamycin (isolated from a *Streptomyces hygroscopicus* bacterium) with FKBP and FRB.

Rapamycin is a molecue isolated from a *Streptomyces hygroscopicus* bacterium and is commercially available. It occupies two distinct hydrophobic pockets, one on FKBP and one on FRB, and binds the two proteins at the same time (FIG. 14).

Construct for Obtaining a HaloTag/FRB Fusion Protein in a Cellular Expression Plasmid A PCR is performed on plasmid pHT2 (Promega) with the following primers:

```
Primer ERV-Nco-HT-s:
5' gcggatatcgccaccatgggatcc 3'
(SEQ ID NO: 4)

Primer HT-PstI-HT-as:
5' acttaattaactgcaggccggccagc 3'
(SEQ ID NO: 5)
```

The PCR is carried out with the polymerase Phusion (Finnzyme) at a hybridization temperature of 72° C.

The PCR product is digested with the enzymes NcoI-PstI for 1 hour at 37° C. and the enzymes are then inactivated at 80° C. for 20 min.

Plasmid pBAD-ST26-FRB, supplied by Covalys, is digested with NcoI and PstI in order to isolate the cassette corresponding to SnapTag (ST26). The linear plasmid obtained, pBAD-FRB, is ligated with the HaloTag PCR product described above.

The ligation is carried out with T4 ligase (Invitrogen). Chemocompetent bacteria called Turbo cells (GenetherapySystem) are transformed with the ligation product. The transformed bacteria are plated on an LB-agar medium (Sigma)+0.1 mg/ml ampicillin (Eurogentec) to allow selection of the bacteria that possess the plasmid.

The plasmid obtained, pBAD-HT-FRB, is purified on a column (QIAGEN) and checked by sequencing.

The cassette corresponding to the coding sequence of the HaloTag(HT)/FRB fusion protein is amplified by PCR from the pBAD-HT-FRB matrix with the following primers:

```
Primer ERV-Nco-HT-s:
5' gcggatatcgccaccatgggatcc 3'
(SEQ ID NO: 4)

Primer pBAD rev:
5' gttctgatttaatctgtatca 3'
(SEQ ID NO: 6)
```

The PCR is carried out with the polymerase Phusion (Finnzyme) at a hybridization temperature of 72° C.

The PCR product is digested with the enzymes EcoRV-AscI for 1 h at 37° C. and the enzymes are then inactivated at 65° C. for 20 min.

The digested PCR product is transferred onto cellular expression plasmid pSEM-XT (Covalys) which has been digested with EcoRV and AscI.

The ligation is carried out with T4 ligase (Invitrogen). Chemocompetent bacteria called Turbo cells (GenetherapySystem) are transformed with the ligation product. The transformed bacteria are plated on an LB-agar medium (Sigma)+ 0.1 mg/ml ampicillin (Eurogentec) to allow selection of the bacteria that possess the plasmid.

The plasmid DNA is obtained by purification on a column (QIAGEN). The integrity of the sequence is verified by sequencing.

Construct for Obtaining a SnapTag/FKBP Fusion Protein in a Cellular Expression Plasmid The cassette corresponding to the coding sequence of the FKBP protein is isolated from Plasmid pBAD-ST-FKBP (Covalys) by PstI-AscI digestion and transferred onto cellular expression plasmid pSEMXT-26 (Covalys).

Ligation is carried out with T4 ligase (Invitrogen). Chemocompetent bacteria called Turbo cells (GenetherapySystem) are transformed with the ligation product. The transformed bacteria are plated on an LB-agar medium (Sigma)+0.1 mg/ml ampicillin (Eurogentec) to allow selection of the bacteria that possess the plasmid.

The plasmid DNA is obtained by purification on columns (QIAGEN). The integrity of the sequence is verified by sequencing.

Cos-7 cells are transitorily transfected with the two plasmid constructs (HaloTag/FRB and SnapTag/FKBP) using lipofectamine 2000 or by electroporation in a 96-well plate at a concentration of 10,000 cells per well.

24 h or 48 h after transitory transfection, the COS-7 cells are incubated for 1 hour with cellular medium containing 5 µM of each substrate specific for the HaloTag and SnapTag enzymes, each of the substrates being covalently bonded to a member of a pair of FRET partners and to a unit that enables it to cross the plasma membrane (manufactured e.g. according to the scheme of FIG. 7 or 8).

After 3 washes with KREBS+0.05% Tween 20, the fluorescence is measured on a RubyStar reader (BMG) before and after induction of the protein interaction with 100 nM of rapamycin (Calbiochem): the TR-FRET signal is significantly higher after incubation with rapamycin.

This Example shows that the method according to the invention makes it possible to reveal a biological interaction in a living cell using the TR-FRET technique.

The invention claimed is:

1. A method of detecting interactions between intracellular biomolecules or a translocation or conformational change of intracellular biomolecules in living cells, comprising the following steps:
- a) labeling a first biomolecule, in a living cell, with a first fluorescent compound having a long fluorescence lifetime, selected from the group consisting of a rare earth chelate and a rare earth cryptate, to produce a first fluorescently labeled biomolecule;
- b) labeling at least one second biomolecule, in said living cell, with a second fluorescent compound, to produce a second fluorescently labeled biomolecule;
- c) subjecting the living cells to a specific stimulation adapted to the biological response to be studied, in the presence or absence of a compound belonging to a bank of test molecules;
- d) subjecting the living cells to a light source whose wavelength excites said first long-lived fluorescent compound;
- e) measuring the intensity of the fluorescence emitted by said first and second fluorescent compounds;
- f) calculating the ratio between the fluorescence intensities of said first fluorescent compound and said second fluorescent compound, or measuring the lifetime of the first or second fluorescent compound; and
- g) comparing the measured signals with those obtained before stimulation of the cells, wherein
said first and at least second fluorescent compounds are time-resolved FRET (TR-FRET) partners;
said first and/or the second biomolecule are each expressed as a fusion protein with a suicide enzyme, and step a) and/or b) are achieved by extracellularly contacting the cell with a substrate for the suicide enzyme, said substrate being covalently bonded to the first or second fluorescent compound, and
at least one of the fluorescent compounds
  (i) is not naturally membrane-permeant
  (ii) is conjugated with a unit that enables it to cross the plasma membrane into the living cell, and
  (iii) is added to the extracellular medium for incubation with the living cells, whereby said the labeling of said intracellular biomolecule with a fluorescent compound that is not naturally membrane-permeant is effected.

2. The method of claim 1, wherein the biomolecule which is not expressed as a fusion protein with a suicide enzyme, if any, is labeled with the fluorescent compounds by using a technique selected from the following: covalent labeling by protein splicing, labeling by expression of a fusion protein comprising the biomolecule and a fluorescent protein as a fluorescent compound, or high-affinity non-covalent labeling via binding partners.

3. The method of claim 1, wherein the fluorescent labeling of the biomolecule which is not expressed as a fusion protein with a suicide enzyme, if any, is effected by coupling the fluorescent compound and the biomolecule respectively with the members of pairs selected from the following: an intein part, a bi-arsenic unit/the sequence Cys-Cys-X-X-Cys-Cys (SEQ ID NO: 1), X representing any amino acid, a metal ion/a polyhistidine sequence, biotin/streptavidin, streptavidin/biotin, bungarotoxin/the tag BTX, cadaverin/the protein sequence PKPQQFM (SEQ ID NO: 2), aziridine/the nucleic sequence TCGA.

4. The method of claim 1, wherein the unit that enables the fluorescent compound to cross the plasma membrane is selected from the following units: esters, polyarginine groups, cholesterol groups, vitamin E groups or aliphatic chains.

5. The method according to claim 1, characterized in that the first fluorescent compound is a rare earth cryptate comprising a pyridine unit.

6. The method of claim 1, wherein the rare earth is terbium or europium.

7. The method of claim 1, wherein the second fluorescent compound is selected from the following compounds: fluorescent proteins, fluorescent proteins extracted from corals, phycobiliproteins or organic fluorescent compounds with a lifetime of less than 100 nanoseconds.

8. The method of claim 7, wherein the second fluorescent compound is an organic fluorescent compound containing a unit that enables it to cross the plasma membrane.

9. The method of claim 1, wherein the unit that enables the fluorescent compound to cross the plasma membrane is selected from pivaloyloxymethyl esters, acetoxymethyl esters or glycolic esters; transportan, undecyl or 1,2-di-O-hexadecylglycerol chains.

10. The method of claim 1, wherein the second fluorescent compound is selected from the green fluorescent protein (GFP), CFP, YFP, B-phycoerythrin, R-phycoerythrin, C-phycocyanin and allo-phycocyanins, XL665 compounds, cyanins, rhodamines, fluoresceins, squarenes and BODIPYs (difluoroboradiazaindacenes).

* * * * *

UNITED STATES PATENT AND TRADEMARK OFFICE
CERTIFICATE OF CORRECTION

PATENT NO. : 8,470,523 B2  
APPLICATION NO. : 12/065706  
DATED : June 25, 2013  
INVENTOR(S) : Pribilla et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1033 days.

Signed and Sealed this

Eighth Day of September, 2015

Michelle K. Lee
*Director of the United States Patent and Trademark Office*